US012740750B2

(12) United States Patent
Badie et al.

(10) Patent No.: US 12,740,750 B2
(45) Date of Patent: Sep. 22, 2026

(54) METHODS AND SYSTEMS FOR ARRHYTHMIA EPISODE PRIORITIZATION AND IMPROVING ARRHYTHMIA DETECTION AND CLASSIFICATION TO REDUCE CLINICAL REVIEW BURDEN

(71) Applicant: Pacesetter, Inc., Sylmar, CA (US)

(72) Inventors: Nima Badie, Oakland, CA (US); Fujian Qu, San Jose, CA (US); Leyla Sabet, Los Angeles, CA (US); Fady Dawoud, Studio City, CA (US); Kevin Davis, Thousand Oaks, CA (US); Christopher Gloschat, Salt Lake City, UT (US); Aditya Goil, Stevenson Ranch, CA (US); Mostafa Sadeghi, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 135 days.

(21) Appl. No.: 18/960,008

(22) Filed: Nov. 26, 2024

(65) Prior Publication Data

US 2025/0082274 A1 Mar. 13, 2025

Related U.S. Application Data

(63) Continuation of application No. 17/738,951, filed on May 6, 2022, now Pat. No. 12,186,100.

(Continued)

(51) Int. Cl.
*A61B 5/00* (2006.01)
*A61B 5/283* (2021.01)

(Continued)

(52) U.S. Cl.
CPC ............ *A61B 5/686* (2013.01); *A61B 5/0031* (2013.01); *A61B 5/283* (2021.01); *A61B 5/352* (2021.01); *A61B 5/361* (2021.01); *A61B 5/363* (2021.01)

(58) Field of Classification Search
CPC ....... A61B 5/686; A61B 5/0031; A61B 5/283; A61B 5/352; A61B 5/361; A61B 5/363; A61B 5/30–5/308; A61B 5/318–367
See application file for complete search history.

(56) References Cited

U.S. PATENT DOCUMENTS 6,589,187 B1 7/2003 Dirnberger
7,212,850 B2 5/2007 Prystowsky et al.

(Continued)

OTHER PUBLICATIONS

Heel, Laura Van, et al., "Abstract 11830: New Algorithms Reduce Clinician Review Burden and Maintain Diagnostic Yield for Repetitive ECGs in Insertable Cardiac Monitors," Circulation, Nov. 11, 2019, 6 pages.

(Continued)

*Primary Examiner* — Jonathan T Kuo
(74) *Attorney, Agent, or Firm* — Pearl Cohen LLP

(57) ABSTRACT

Embodiments reduce burden associated with analyzing EGM segments obtained from an IMD that monitors for arrhythmic episodes. Respective EGM data and respective classification data is obtained for each arrhythmic episode detected by the IMD during a period of time. A representative R-R interval or HR for each of the arrhythmic episodes is determine by the IMD, wherein a manner for determining the representative R-R interval or HR depends on the type of the arrhythmic episode, such that for at least two different types of arrhythmic episodes the manners differ. An external system (ES) obtains data from the IMD, directly or indirectly, and selects arrhythmic episode(s) for which corresponding EGM segments are to be displayed for each type (Continued)

of arrhythmic episode, wherein the selecting is performed based on the representative R-R intervals or HRs determined by the IMD for the arrhythmic episodes. Additional and alternative embodiments are also described herein.

22 Claims, 6 Drawing Sheets

Related U.S. Application Data

(60) Provisional application No. 63/186,673, filed on May 10, 2021.

(51) Int. Cl.
*A61B 5/352* (2021.01)
*A61B 5/361* (2021.01)
*A61B 5/363* (2021.01)

(56) References Cited

U.S. PATENT DOCUMENTS 7,353,063 B2 4/2008 Simms, Jr.
7,634,310 B2 12/2009 Lee et al.
7,738,950 B2 6/2010 Johnson et al.
7,907,996 B2 3/2011 Prystowsky et al.
8,064,992 B2 11/2011 Henry et al.
8,200,322 B2 6/2012 Ousdigian et al.
8,200,324 B2 6/2012 Shen et al.
8,521,269 B1 8/2013 Gunderson et al.
8,588,895 B2 11/2013 Sanghera et al.
8,620,418 B1 12/2013 Kuppuraj et al.
8,744,560 B2 * 6/2014 Gunderson ........ A61N 1/37247 600/518
8,798,734 B2 8/2014 Kuppuraj et al.
8,945,019 B2 2/2015 Prystowsky et al.
9,081,884 B2 7/2015 Kuppuraj et al.
9,668,668 B2 6/2017 Gunderson et al.
11,207,015 B2 * 12/2021 Kuppuraj ............. A61B 5/0006
2002/0077561 A1 6/2002 Jamar et al.
2008/0270036 A1 10/2008 Webb et al.
2010/0106036 A1 4/2010 Dong et al.
2013/0085403 A1 4/2013 Gunderson
2013/0085406 A1 * 4/2013 Gunderson ........ A61N 1/37247 600/518
2019/0387991 A1 * 12/2019 Kuppuraj ............. A61B 5/0006
2022/0354427 A1 11/2022 Badie et al.

OTHER PUBLICATIONS

Notice of Allowance dated Sep. 5, 2024, U.S. Appl. No. 17/738,951, filed May 6, 2022.
Post Allowance Amendment under 37 CFR §1.312 dated Nov. 11, 2024, U.S. Appl. No. 17/738,951, filed May 6, 2022.

* cited by examiner

METHODS AND SYSTEMS FOR ARRHYTHMIA EPISODE PRIORITIZATION AND IMPROVING ARRHYTHMIA DETECTION AND CLASSIFICATION TO REDUCE CLINICAL REVIEW BURDEN

PRIORITY CLAIM

This application is a continuation of U.S. patent application Ser. No. 17/738,951, filed May 6, 2022, titled METHODS AND SYSTEMS FOR ARRHYTHMIA EPISODE PRIORITIZATION AND IMPROVING ARRHYTHMIA DETECTION AND CLASSIFICATION TO REDUCE CLINICAL REVIEW BURDEN, which claims priority to U.S. Provisional Patent Application No. 63/186,673, filed May 10, 2021. Priority is claimed to each of the above applications, and each of the above applications is incorporated herein by reference in its entirety.

FIELD OF THE INVENTION

Embodiments of the present technology described herein relate generally to systems and methods for reducing clinical review burden by managing presentation of electrogram (EGM) segments that correspond to detected arrhythmia episodes.

BACKGROUND OF THE INVENTION

Implantable Cardiac Monitors (ICMs), which are also known as Insertable Cardiac Monitor (ICM) devices, have become an invaluable tool for ambulatory diagnosis of cardiac arrhythmias, remote monitoring of cardiac arrhythmias, and more generally remote patient care. However, one of the challenges with using such devices is deciding how much data should be available to medical personnel (aka clinicians) to manually review in the form of recorded electrogram (EGM) segments. This is at least in part because timely review and adjudication of the EGM segments corresponding to arrhythmia detections, e.g., to identify clinically actionable arrhythmias, require significant resources for device monitoring clinics. Initially, the field was receptive to receiving and reviewing every single EGM segment recorded by an ICM device or other type of IMD. However, as ICM devices became smaller in size and their use increased, clinics began to be inundated with data that did not always have clinical value, e.g., due to redundancy and/or false arrhythmia detections. The recent increase in the number of implanted ICM devices with remote monitoring capability, and corresponding increase in the volume of EGM segments requiring manual adjudication, revealed the need for efficient EGM prioritization tools that do not compromise diagnostic yield. Over time, the consensus among clinics and medical personnel has changed, and depending on the patient type or reason for monitoring and size of the clinic, a preference was adopted to receive less data, despite the potential cost of slight delays in diagnosis.

BRIEF SUMMARY

Certain embodiments of the present technology are related to methods and systems for reducing a burden associated with analyzing electrogram (EGM) segments obtained from an implantable medical device (IMD) that is configured to monitor for arrhythmic episodes of a patient within which the IMD is implanted. In accordance with certain embodiments, a method comprises obtaining respective EGM data and respective classification data for each arrhythmic episode of a plurality of arrhythmic episodes that were detected by the IMD during a period of time, wherein the respective EGM data is indicative of an EGM segment corresponding to the arrhythmic episode, and wherein the respective classification data specifies a type of the arrhythmic episode. The method also comprises obtaining a representative R-R interval or a representative heart rate (HR) for each of the arrhythmic episodes for which respective EGM data and respective classification data were obtained, wherein a manner for determining the representative R-R interval or the representative HR for the arrhythmic episode depends on the type of the arrhythmic episode, and wherein for at least two of the different types of arrhythmic episodes the manners, for determining the representative R-R interval or the representative HR, differ from one another. The method also comprises selecting one or more arrhythmic episodes for which corresponding EGM segments are to be displayed for each type of arrhythmic episode, of the plurality of different types of arrhythmic episodes for which the EGM data and the classification data were obtained for the period of time, wherein the selecting is performed based on the representative R-R intervals or the representative HRs that are determined for the plurality of arrhythmic episodes. Additionally, the method includes providing for display of the EGM segments that correspond to the one or more arrhythmic episodes that were selected for display, for each type of arrhythmic episode, of the plurality of different types of arrhythmic episodes for which the EGM data and the classification data were obtained for the period of time.

In accordance with certain embodiments, the representative R-R interval or the representative HR for each bradycardia type of arrhythmic episode, for which respective EGM data and respective classification data were obtained, comprises a longest R-R interval or a slowest HR during the bradycardia episode.

In accordance with certain embodiments, the representative R-R interval or the representative HR interval for each tachycardia type of arrhythmic episode, for which respective EGM data and respective classification data were obtained, comprises a shortest R-R interval or a fastest HR during the tachycardia episode.

In accordance with certain embodiments, the representative R-R interval or the representative HR interval for each atrial fibrillation (AF) type of arrhythmic episode, for which respective EGM data and respective classification data were obtained, comprises a mean R-R interval or a mean HR during the AF episode.

In accordance with certain embodiments, the representative R-R interval or the representative HR for each cardiac pause type of arrhythmic episode, for which respective EGM data and respective classification data were obtained, comprises a longest R-R interval during the cardiac pause episode or the representative HR that is fastest.

In accordance with certain embodiments, for the bradycardia type arrhythmic episodes, the one or more EGM segments that are selected for display include the EGM segment having the representative R-R interval that is shortest or the representative HR that is fastest.

In accordance with certain embodiments, for the tachycardia type arrhythmic episodes, the one or more EGM segments that are selected for display include the EGM segment having the representative R-R interval that is shortest or the representative HR that is fastest.

In accordance with certain embodiments, for the cardiac pause type episodes, the one or more EGM segments that are selected for display include the EGM segment having the representative R-R interval that is shortest or the representative HR that is fastest.

In accordance with certain embodiments, for the AF type arrhythmic episodes, the one or more EGM segments that are selected for display include the EGM segment having the representative R-R interval that is shortest or the representative HR that is fastest.

In accordance with certain embodiments, a method also includes obtaining a respective duration of each of the arrhythmic episodes for which respective EGM data and respective classification data were obtained. In certain such embodiments, the step of selecting one or more arrhythmic episodes for which corresponding EGM segments are to be displayed for each type of arrhythmic episode, of the plurality of different types of arrhythmic episodes for which the EGM data and the classification data were obtained for the period of time, also comprises selecting, for each type of arrhythmic episode, one or two of the arrhythmic episodes having the longest duration(s).

In accordance with certain embodiments, one of the methods summarized above is performed by a non-implanted system, and the respective EGM data, the respective classification data, the representative R-R interval or the representative HR, and the respective duration, for each arrhythmic episode of the plurality of arrhythmic episodes that were detected by the IMD during the period of time, are obtained by the non-implanted system from the IMD.

In accordance with certain embodiments, one of the methods summarized above also includes saving the respective EGM data and the respective classification data for each arrhythmic episode of the plurality of arrhythmic episodes that were detected by the IMD during the period of time, but were not selected for display at the selecting step. Additionally, the method includes enabling a user to select one or more additional arrhythmic episodes for which corresponding EGM segments are to be displayed for at least one type of arrhythmic episode, of the plurality of different types of arrhythmic episodes for which the EGM data and the classification data were obtained for the period of time, and providing for displaying of EGM segments that correspond to the one or more additional arrhythmic episodes that were selected for display by the user.

A system, according to certain embodiments of the present technology, comprises a telemetry subsystem that is non-implanted and is configured to communicate with an IMD. The system also includes one or more processors, one or more of which can be included in the IMD, and one or more of which can be non-implanted. The telemetry subsystem is configured to obtain respective EGM data for each arrhythmic episode of a plurality of arrhythmic episodes that were detected by the IMD during a period of time, wherein the respective EGM data is indicative of an EGM segment corresponding to the arrhythmic episode. The telemetry subsystem, or at least one of the one or more processors, is/are configured to obtain respective classification data for each arrhythmic episode of the plurality of arrhythmic episodes that were detected by the IMD during the period of time, wherein the respective classification data specifies a type of the arrhythmic episode. The telemetry subsystem, or at least one of the one or more processors, is/are also configured to obtain a representative R-R interval or a representative heart rate (HR) for each of the arrhythmic episodes for which respective EGM data and respective classification data were obtained, wherein a manner for determining the representative R-R interval or the representative HR for the arrhythmic episode depends on the type of the arrhythmic episode, and wherein for at least two of the different types of arrhythmic episodes the manners (for determining the representative R-R interval or the representative HR) differ from one another. In accordance with certain embodiments, at least one of the one or more processors selects the one or more arrhythmic episodes for which corresponding EGM segments are to be displayed, for each type of arrhythmic episode, based on the representative R-R intervals or the representative HRs that are determined for the plurality of arrhythmic episodes. At least one of the one or more processors is/are also configured to cause displaying of the EGM segments that correspond to the one or more arrhythmic episodes that were selected for display, for each type of arrhythmic episode, of the plurality of different types of arrhythmic episodes for which the EGM data and the classification data were obtained for the period of time.

In accordance with certain embodiments, at least one of the one or more processors is configured to determine that the representative R-R interval or the representative HR for each bradycardia type of arrhythmic episode, for which respective EGM data and respective classification data were obtained, comprises a longest R-R interval or a slowest HR during the bradycardia episode.

In accordance with certain embodiments, at least one of the one or more processors is configured to determine that the representative R-R interval or the representative HR interval for each tachycardia type of arrhythmic episode, for which respective EGM data and respective classification data were obtained, comprises a shortest R-R interval or a fastest HR during the tachycardia episode.

In accordance with certain embodiments, at least one of the one or more processors is configured to determine that the representative R-R interval or the representative HR interval for each atrial fibrillation (AF) type of arrhythmic episode, for which respective EGM data and respective classification data were obtained, comprises a mean R-R interval or a mean HR during the AF episode.

In accordance with certain embodiments, at least one of the one or more processors is configured to determine that the representative R-R interval or the representative HR for each cardiac pause type of arrhythmic episode, for which respective EGM data and respective classification data were obtained, comprises a longest R-R interval during the cardiac pause episode or the representative HR that is fastest.

In accordance with certain embodiments, at least one of the one or more processors is configured to select for display: for the bradycardia type arrhythmic episodes, the one or more EGM segments that include the EGM segment having the representative R-R interval that is shortest or the representative HR that is fastest; for the tachycardia type arrhythmic episodes, the one or more EGM segments that include the EGM segment having the representative R-R interval that is shortest or the representative HR that is fastest; for the cardiac pause type episodes, the one or more EGM segments that include the EGM segment having the representative R-R interval that is shortest or the representative HR that is fastest; and for the AF type arrhythmic episodes, the one or more EGM segments that include the EGM segment having the representative R-R interval that is shortest or the representative HR that is fastest.

In accordance with certain embodiments, the telemetry subsystem, or at least one of the one or more processors, is configured to obtain a respective duration of each of the arrhythmic episodes for which respective EGM data and respective classification data were obtained for the period of time. In certain such embodiments, at least one of the one or more processors is configured include in the one or more arrhythmic episodes for which corresponding EGM segments are selected to be displayed for each type of arrhythmic episode.

In accordance with certain embodiments, the telemetry subsystem that is non-implanted obtains from the IMD, via a communications link, the respective EGM data, the respective classification data, the representative R-R interval or the representative HR, and the respective duration, for each arrhythmic episode of the plurality of arrhythmic episodes that were detected by the IMD during the period of time.

In accordance with certain embodiments, one of the above summarized systems also includes data storage configured to save the respective EGM data and the respective classification data for each arrhythmic episode of the plurality of arrhythmic episodes that were detected by the IMD during the period of time, but were not selected for display. In certain such embodiments, at least one of the one or more processors is/are configured to enable a user to select one or more additional arrhythmic episodes for which corresponding EGM segments are to be displayed for at least one type of arrhythmic episode, of the plurality of different types of arrhythmic episodes for which the EGM data and the classification data were obtained for the period of time, and cause displaying of EGM segments that correspond to the one or more additional arrhythmic episodes that were selected for display by the user.

A method according to another embodiment of the present technology comprises obtaining respective EGM data and respective classification data for each arrhythmic episode of a plurality of arrhythmic episodes that were detected by the IMD during a period of time, wherein the respective EGM data is indicative of an EGM segment corresponding to the arrhythmic episode, and wherein the respective classification data specifies a type of the arrhythmic episode. The method also includes ranking the arrhythmic episodes for each type of arrhythmic episode, of the plurality of different types of arrhythmic episodes for which the EGM data and the classification data were obtained for the period of time, wherein the ranking is performed using rules. Additionally, the method includes selecting, based on results of the ranking, one or more arrhythmic episodes for which corresponding EGM segments are to be displayed for each type of arrhythmic episode, of the plurality of different types of arrhythmic episodes for which the EGM data and the classification data were obtained for the period of time. Further, the method includes providing for display of EGM segments that correspond to the one or more arrhythmic episodes that were selected for display, for each type of arrhythmic episode, of the plurality of different types of arrhythmic episodes for which the EGM data and the classification data were obtained for the period of time. The rules that are used for the ranking are used to produce respective ranking scores for the plurality of arrhythmic episodes that were detected by the IMD during the period of time.

In accordance with certain embodiments, the rules, that are used to produce the ranking score for the arrhythmic episode, produce the ranking score based on at least one of the following: a degree of noise in the EGM segment that corresponds to the arrhythmic episode; a proximity of the arrhythmic episode to one or more noise interruptions; an extent of R-wave undersensing during the arrhythmic episode; an extent of at least one of P-wave or T-wave oversensing during the arrhythmic episode; an extent of similarity between the EGM segment that corresponds to the arrhythmic episode that was classified as a specific type of arrhythmic episode, and a previously adjudicated EGM segment determined to actually correspond to the specific type of arrhythmic episode; an extent of similarity between the EGM segment that corresponds to the arrhythmic episode that was classified as a specific type of arrhythmic episode, and a previously adjudicated EGM segment determined to not actually correspond to the specific type of arrhythmic episode; a time of day when the arrhythmic episode occurred; and a level of variation in an amplitude of the EGM segment that corresponds to the arrhythmic episode.

In accordance with certain embodiments, one of the above summarized methods also includes saving the respective EGM data and the respective classification data for each arrhythmic episode of the plurality of arrhythmic episodes that were detected by the IMD during the period of time, but were not selected for display at the selecting step; enabling a user to select one or more additional arrhythmic episodes for which corresponding EGM segments are to be displayed for at least one type of arrhythmic episode, of the plurality of different types of arrhythmic episodes for which the EGM data and the classification data were obtained for the period of time; and providing for display of EGM segments that correspond to the one or more additional arrhythmic episodes that were selected for display by the user.

A system according to another embodiments comprises a telemetry subsystem that is non-implanted and is configured to communicate with the IMD, and one or more processors, one or more of which can be included in the IMD, and one or more of which can be non-implanted. The telemetry subsystem is configured to obtain respective EGM data for each arrhythmic episode of a plurality of arrhythmic episodes that were detected by the IMD during a period of time, wherein the respective EGM data is indicative of an EGM segment corresponding to the arrhythmic episode. The telemetry subsystem, or at least one of the one or more processors, is/are configured to obtain respective classification data for each arrhythmic episode of the plurality of arrhythmic episodes that were detected by the IMD during the period of time, wherein the respective classification data specifies a type of the arrhythmic episode. At least one of the one or more processors, is/are configured to rank the arrhythmic episodes for each type of arrhythmic episode, of the plurality of different types of arrhythmic episodes for which the EGM data and the classification data were obtained for the period of time, wherein the ranking is performed using rules. At least one of the one or more processors, is/are also configured to select, based on results of the ranking, one or more arrhythmic episodes for which corresponding EGM segments are to be displayed for each type of arrhythmic episode, of the plurality of different types of arrhythmic episodes for which the EGM data and the classification data were obtained for the period of time. At least one of the one or more processors, is/are also configured to cause displaying of EGM segments that correspond to the one or more arrhythmic episodes that were selected for display, for each type of arrhythmic episode, of the plurality of different types of arrhythmic episodes for which the EGM data and the classification data were obtained for the period of time. The rules that are used for the ranking are used to produce respective ranking scores for the plurality of arrhythmic episodes that were detected by the IMD during the period of time. In accordance with certain embodiments, the rules produce the ranking scores based on at least one of the following: a degree of noise in the EGM segment that corresponds to the arrhythmic episode; a proximity of the arrhythmic episode to one or more noise interruptions; an extent of R-wave undersensing during the arrhythmic episode; an extent of at least one of P-wave or T-wave oversensing during the arrhythmic episode; an extent of similarity between the EGM segment that corresponds to the arrhythmic episode that was classified as a specific type of arrhythmic episode, and a previously adjudicated EGM segment determined to actually correspond to the specific type of arrhythmic episode; an extent of similarity between the EGM segment that corresponds to the arrhythmic episode that was classified as a specific type of arrhythmic episode, and a previously adjudicated EGM segment determined to not actually correspond to the specific type of arrhythmic episode; a time of day when the arrhythmic episode occurred; and a level of variation in an amplitude of the EGM segment that corresponds to the arrhythmic episode.

In accordance with certain embodiments, one of the above summarized systems also includes data storage configured to save the respective EGM data and the respective classification data for each arrhythmic episode of the plurality of arrhythmic episodes that were detected by the IMD during the period of time, but were not already selected for display. In certain such embodiments, at least one of the one or more processors is/are configured to enable a user to select one or more additional arrhythmic episodes for which corresponding EGM segments are to be displayed, and cause displaying of EGM segments that correspond to the one or more additional arrhythmic episodes that were selected for display by the user.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

DETAILED DESCRIPTION

Figure 1A:
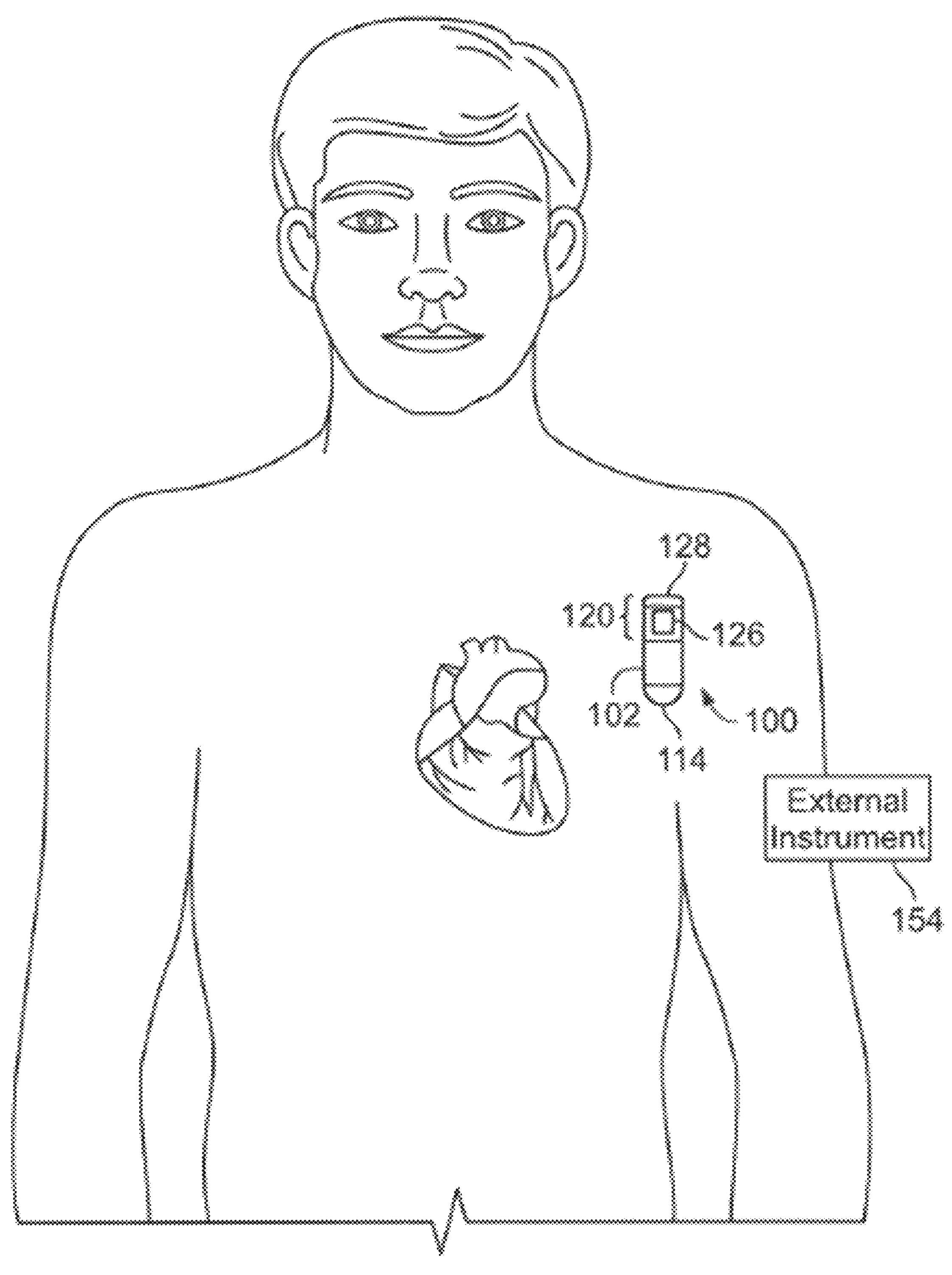
FIG. 1A illustrates an example ICM intended for subcutaneous implantation at a site near the heart.

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle.

Rhythms that do not follow the sequence of events described above are known as arrhythmias. Those that result in a heart rate slower than normal are known as bradyarrhythmias or bradycardias. Those that result in a faster heart rate than normal are called tachyarrhythmias or tachycardias. Tachyarrhythmias (aka tachycardias) are further classified as supraventricular tachycardias (SVTs) and ventricular tachycardias (VTs). VTs are heart rhythm disorders (arrhythmias) caused by abnormal electrical signals in the ventricles, which are the lower chambers of the heart. SVTs, by contrast, are generally characterized by abnormal heart rhythms that arise in the atria, which are the upper chambers of the heart, or the atrioventricular node (AV node). Additionally, there are various types of different SVTs and various types of VTs that can be characterized. For example, a paroxysmal SVT can exhibit heart rates between approximately 140 beats per minute (bpm) and approximately 250 bpm. However, the most common SVTs are typically atrial flutter (AFL) and atrial fibrillation (AF). In addition, many SVTs involve the AV node, for example, AV nodal reentry tachycardia (AVNRT) where an electrical loop or circuit includes the AV node. Another type of SVT is an AV reentrant tachycardia (AVRT), where an AV reentrant circuit typically involves the AV node and an aberrant conducting bundle known as an accessory pathway that connects a ventricle to an atrium.

Atrial flutter (AFL) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure (HF) as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing AF. AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained VT can lead to VF. In sustained VT, consecutive impulses arise from the ventricles at a rate of 100 bpm or more. Such activity may degenerate further into disorganized electrical activity known as VF. In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia. Further, there are various different types of VT, including, e.g., monomorphic VT and polymorphic VT, for which different types of therapy may be appropriate.

Cardiac pause, also known as asystole, refers to a delay between ventricular contractions, identified by R-waves in an EGM, that exceeds a specified time threshold, e.g., 3 seconds. Cardiac pause may coincide with syncope, also known as fainting, which is a temporary loss of consciousness. For example, if an R-R interval exceeds a time threshold (e.g., 3 seconds), a cardiac pause may have occurred, which may be the underlying cause of syncope for a patient. Pacing therapy is one type of treatment that can be used to reduce and preferably prevent cardiac pauses.

Since their inception, ICMs have quickly been established as an invaluable tool for ambulatory diagnosis of various types of cardiac arrhythmias, such as AF, tachycardias, bradycardia, and asystole. However, as noted above, one of the challenges with using such devices is deciding how much data should be made available to medical personnel (aka clinicians) to review in the form of recorded EGM segments. Certain embodiments of the present technology, which are described below, can be used to reduce clinical review burden by managing presentation of EGM segments that correspond to detected arrhythmia episodes and improving arrhythmia detections and classifications. Managing the presentation of EGM segments, as will be described below, can involve ranking (aka prioritizing) EGM segments and selecting a subset of the obtained EGM segments (e.g., the highest ranking or prioritized) EGM segments to display to medical personnel, which reduces clinical burden by reducing how many EGM segments are manually reviewed by the medical personnel. Improving arrhythmia detections and classifications can also reduce clinical burden, for example, by reducing how many false positives are manually reviewed by the medical personnel.

Prior to providing details of the specific embodiments of the present technology, an example ICM, or more generally system, with which embodiments of the present technology can be used will first be described with reference to FIGS. 1A and 1B. However, it should be noted that embodiments of the present technology are not limited to use with the ICM described below, and in fact, are not limited to use with ICMs. Rather, embodiments of the present technology, as well be explained in further detail below, can be used with various other types of IMDs besides ICMs, such as, but not limited to, implantable pacemakers and implantable cardioverter defibrillators (ICDs). Pacemakers can be conventional pacemakers that include one or more leads that are used for sensing and/or pacing in one or more cardiac chambers, or can be leadless pacemakers. ICDs can be transvenous ICDs are subcutaneous ICDs (S-ICDs). For most of the following description, embodiments of the present technology will be described as being used with an ICM type of IMD. However, as just explained above, embodiments of the present technology can also be used with other types of IMDs, examples of which were mentioned above.

FIG. 1A illustrates an example ICM 100 intended for subcutaneous implantation at a site near the heart. The ICM 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the ICM 100, while the electrode 126 is located on a proximal side of the ICM 100. Additionally or alternatively, electrodes 114, 126 may be located on opposite sides of the ICM 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.). The housing 102 includes various other components such as: sense electronics for receiving signals from the electrodes, a microprocessor for processing the signals in accordance with algorithms, such as the arrhythmia detection algorithms, a loop memory for temporary storage of EGM data, a device memory for long-term storage of EGM data upon certain triggering events, such as an arrhythmia detection, sensors for detecting patient activity and a battery for powering components.

In at least some embodiments, the ICM 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The ICM 100 may be configured to be activated by the patient or automatically activated, in connection with recording EGM signals.

The ICM 100 senses EGM signals, processes the EGM signals to detect arrhythmias and if an arrhythmia is detected, automatically records the portions of EGM signals in memory for subsequent transmission to an external device. The EGM signal processing and arrhythmia detection is provided for, at least in part, by algorithms embodied in or implemented by the microprocessor. The ICM 100 includes one or more processors and memory that stores program instructions directing the processors to implement arrhythmia detections utilizing an on-board processes that analyzes cardiac activity signals (e.g., EGM signals) collected over one or more sensing channels.

Figure 1B:
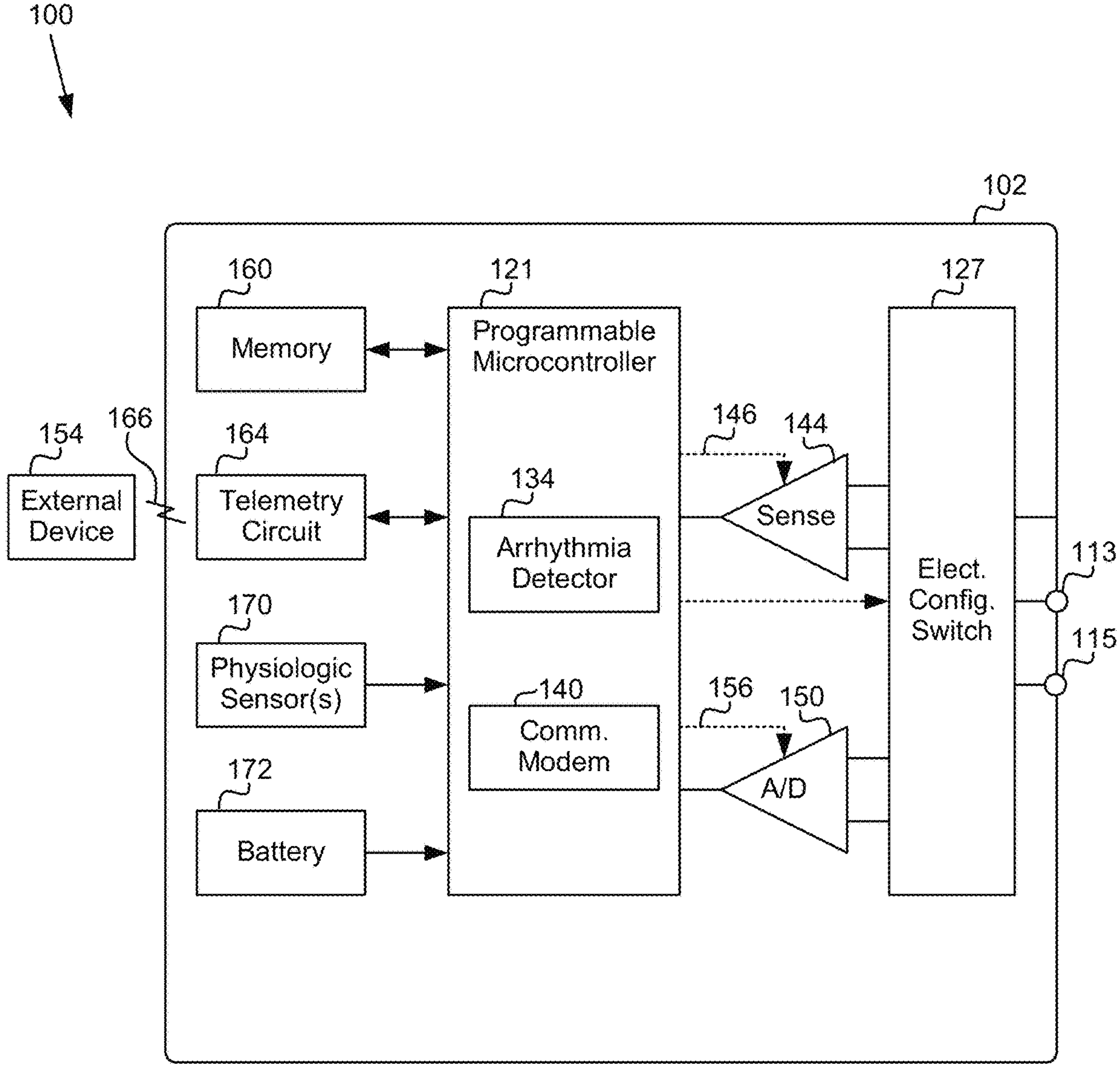
FIG. 1B shows a block diagram of the ICM 100 formed in accordance with certain embodiments herein.

FIG. 1B shows a block diagram of the ICM 100 formed in accordance with embodiments herein. The ICM 100 may be implemented to monitor ventricular activity alone, or both ventricular and atrial activity through sensing circuit. The ICM 100 has a housing 102 to hold the electronic/computing components. The housing 102 (which is often referred to as the "can", "case", "encasing", or "case electrode") may be programmably selected to act as an electrode for certain sensing modes. Housing 102 further includes a connector (not shown) with at least one terminal 113 and optionally additional terminals 115. The terminals 113, 115 may be coupled to sensing electrodes that are provided upon or immediately adjacent the housing 102. Optionally, more than two terminals 113, 115 may be provided in order to support more than two sensing electrodes, such as for a bipolar sensing scheme that uses the housing 102 as a reference electrode. Additionally or alternatively, the terminals 113, 115 may be connected to one or more leads having one or more electrodes provided thereon, where the electrodes are located in various locations about the heart. The type and location of each electrode may vary.

The ICM 100 includes a programmable microcontroller 121 that controls various operations of the ICM 100, including cardiac monitoring. Microcontroller 121 includes a microprocessor (or equivalent control circuitry), RAM and/or ROM memory, logic and timing circuitry, state machine circuitry, and I/O circuitry. The microcontroller 121 also performs the operations described herein in connection with collecting cardiac activity data and analyzing the cardiac activity data.

A switch 127 is optionally provided to allow selection of different electrode configurations under the control of the microcontroller 121. The electrode configuration switch 127 may include multiple switches for connecting the desired electrodes to the appropriate I/O circuits, thereby facilitating electrode programmability. The switch 127 is controlled by a control signal from the microcontroller 121. Optionally, the switch 127 may be omitted and the I/O circuits directly connected to the housing electrode 114 and a second electrode 126.

Microcontroller 121 includes an arrhythmia detector 134 that is configured to analyze cardiac activity signals to identify potential arrhythmia episodes (e.g., tachycardias, bradycardias, cardia pause, AF, etc.). By way of example, the arrhythmia detector 134 may implement an arrhythmia detection algorithm as described in U.S. Pat. No. 8,135,456, the complete subject matter of which is incorporated herein by reference. Although not shown, the microcontroller 121 may further include other dedicated circuitry and/or firmware/software components that assist in monitoring various conditions of the patient's heart and managing pacing therapies. The arrhythmia detector 134 of the microcontroller 121 includes an on-board arrhythmia detection processes that detects arrhythmia episodes, such as AF episodes using R-R interval irregularities. The arrhythmia detector 124 may be implemented as firmware, software and/or circuits.

The arrhythmia detector 134 analyzes an EGM signal sensed using electrodes in order to detect arrhythmic episodes, which can also be referred to interchangeably as an arrhythmia episode or an episode of an arrhythmia. More specifically, where an IMD is an ICM that senses a far field EGM signal, the ICM can analyze a sensed far field EGM signal sensed along a sensing vector between a combination of electrodes for one or more beats. The arrhythmia detector 134 identifies one or more features of interest from the EGM signals, and based on further analysis of the features of interest determines whether the EGM signals are indicative of a normal sinus rhythm or an arrhythmia episode. When an arrhythmia episode is identified, the arrhythmia detector 134 can generate one or more markers that are temporally aligned with corresponding features of interest in the EGM signals, or more specifically, segments thereof. Such markers refer to data and/or information identified from EGM signals that may be presented as graphical and/or numeric indicia indicative of one or more features within the EGM signals and/or indicative of one or more episodes exhibited by the cardiac events. Markers may be superimposed upon EGM signals or presented proximate to, and temporally aligned with, EGM signals or segments thereof. Non-limiting examples of markers may include R-wave markers, noise markers, activity markers, interval markers, refractory markers, P-wave markers, T-wave markers, PVC markers, sinus rhythm markers, AF markers and other arrhythmia markers. As further nonlimiting examples, basic event markers may include "AF entry" to indicate a beginning of an AF event, "in AF" to indicate that AF is ongoing, "AF exit" to indicate that AF has terminated, "T" to indicate a tachycardia beat, "B" to indicate a bradycardia beat, "A" to indicate an asystole beat, "VS" to indicate a regular sinus beat, "Tachy" to indicate a tachycardia episode, "Brady" to indicate a Bradycardia episode, "Asystole" to indicate an asystole episode, "Patient activated" to indicate a patient activated episode. An activity marker may indicate activity detected by activity sensor (e.g., accelerometer) during the EGM signal. Noise markers may indicate entry/start, ongoing, recovery and exit/stop of noise. Markers may be presented as symbols, dashed lines, numeric values, thickened portions of a waveform, and the like. Markers may represent events, intervals, refractory periods, ICM activity, and other algorithm related activity. For example, interval markers, such as the R-R interval, may include a numeric value indicating the duration of the interval. The AF markers indicate atrial fibrillation rhythmic.

In accordance with certain embodiments, in response to the arrhythmia detector 134 detecting and classifying an arrhythmia, the arrhythmia detector 134 (or more generally, the IMD) forms a device classified arrhythmia (DCA) data set associated with the classified arrhythmia episode and stores the DCA data set in the memory 160 of the IMD. The DCA data set for an arrhythmia episode can include respective EGM data and respective classification data for the arrhythmia episode. The respective EGM data can be indicative of an EGM segment corresponding to the arrhythmic episode, and the respective classification data can specify the type of the arrhythmic episode. Such EGM data can include temporal (e.g., morphological) information and frequency information about the EGM segment, which information enables the EGM segment to be reproduced for display to medical personal, and enables the EGM segment to be analyzed, e.g., for the purpose of ranking the arrhythmia episode corresponding to the EGM segment, determining whether the arrhythmia detection was a true positive or a false positive detection, determining whether the arrhythmia episode should be reclassified is being a different type of arrhythmia than originally classified, and/or the like. Examples of the types of arrhythmias that may be specified by the respective classification data were described above. The DCA data for an arrhythmia episode can also include respective marker data for one or more of the markers described above, but not limited thereto. Where an ICM or other type of IMD detects an arrhythmic episode, it can be said that a detection of the arrhythmic episode was triggered by the IMD.

The ICM 100 is further equipped with a communication modem (modulator/demodulator) 140 to enable wireless communication. In one implementation, the communication modem 140 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 140 may be implemented in hardware as part of the microcontroller 121, or as software/ firmware instructions programmed into and executed by the microcontroller 121. Alternatively, the modem 140 may reside separately from the microcontroller as a standalone component. The modem 140 facilitates data retrieval from a remote monitoring network. The modem 140 enables timely and accurate data transfer directly from the patient to an electronic device utilized by a physician.

The ICM 100 includes sensing circuit 144 selectively coupled to one or more electrodes that perform sensing operations, through the switch 127 to detect cardiac activity data indicative of cardiac activity. The sensing circuit 144 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 127 may be used to determine the sensing polarity of the cardiac signal by selectively closing the appropriate switches.

The output of the sensing circuit 144 is connected to the microcontroller 121 which, in turn, determines when to store EGM data for a segment of an EGM signal (digitized by the A/D data acquisition system 150) in the memory 160. For example, the microcontroller 121 may only store the EGM data (from the A/D data acquisition system 150) in the memory 160 when a potential arrhythmia episode is detected. The sensing circuit 144 receives a control signal 146 from the microcontroller 121 for purposes of controlling the gain, threshold, polarization charge removal circuitry (not shown), and the timing of any blocking circuitry (not shown) coupled to the inputs of the sensing circuit.

Optionally, the ICM 100 may include multiple sensing circuits, similar to sensing circuit 144, where each sensing circuit is coupled to two or more electrodes and controlled by the microcontroller 121 to sense cardiac electrical activity detected at the corresponding two or more electrodes. The sensing circuit 144 may operate in a unipolar sensing configuration or in a bipolar sensing configuration. Optionally, the sensing circuit 144 may be removed entirely and the microcontroller 121 perform the operations described herein based upon the EGM signals from the A/D data acquisition system 150 directly coupled to the electrodes.

The ICM 100 further includes an analog-to-digital A/D data acquisition system (DAS) 150 coupled to one or more electrodes via the switch 127 to sample cardiac activity signals across any pair of desired electrodes. The data acquisition system 150 is configured to acquire cardiac electrogram (EGM) signals (or segments thereof), convert the raw analog data into digital data, and store the digital data as EGM data for later processing and/or telemetric transmission to an external device 154 (e.g., a programmer, local transceiver, or a diagnostic system analyzer). The data acquisition system 150 is controlled by a control signal 156 from the microcontroller 121. The EGM signals may be utilized as the cardiac activity data that is analyzed for potential arrhythmia episodes. The arrhythmia detection algorithms may be applied to EGM signals from the sensing circuit 144 and/or the DAS 150.

By way of example, the external device 154 may represent a bedside monitor installed in a patient's home and utilized to communicate with the ICM 100 while the patient is at home, in bed or asleep. The external device 154 may be a programmer used in a clinic to interrogate the ICM 100, retrieve data and program detection criteria and other features. The external device 154 may be a handheld device (e.g., smartphone, tablet device, laptop computer, smartwatch and the like) that can be coupled over a network (e.g., the Internet) to a remote monitoring service, medical network and the like. The external device 154 facilitates access by clinicians to patient data as well as permitting the physician to review real-time EGM signals sensed by the ICM 100.

The microcontroller 121 is coupled to a memory 160 by a suitable data/address bus 162. The programmable operating parameters used by the microcontroller 121 are stored in memory 160 and used to customize the operation of the ICM 100 to suit the needs of a particular patient. Such operating parameters define, for example, detection rate thresholds, sensitivity, automatic features, arrhythmia detection criteria, activity sensing or other physiological sensors, and electrode polarity, etc.

In addition, the memory 160 stores the cardiac activity data, as well as the markers and other data content associated with detection of arrhythmia episodes. The operating parameters of the ICM 100 may be non-invasively programmed into the memory 160 through a telemetry circuit 164 in telemetric communication via communication link 166 with the external device 154. The telemetry circuit 164 allows EGM data, classification data, etc. and status information relating to the operation of the ICM 100 (as contained in the microcontroller 121 or memory 160) to be sent to the external device 154 through the established communication link 166. In accordance with embodiments herein, the telemetry circuit 164 conveys the DCA data sets and other information related to arrhythmia episodes to an external device.

The ICM 100 may further include magnet detection circuitry (not shown), coupled to the microcontroller 121, to detect when a magnet is placed over the unit. A magnet may be used by a clinician to perform various test functions of the housing 102 and/or to signal the microcontroller 121 that the external device 154 is in place to receive or transmit data to the microcontroller 121 through the telemetry circuits 164.

The ICM 100 can further include one or more physiologic sensors 170. Such sensors are commonly referred to (in the pacemaker arts) as "rate-responsive" or "exercise" sensors. The physiological sensor 170 may further be used to detect changes in the physiological condition of the heart, or diurnal changes in activity (e.g., detecting sleep and wake states). Signals generated by the physiological sensors 170 are passed to the microcontroller 121 for analysis and optional storage in the memory 160 in connection with the cardiac activity data, markers, episode information and the like. While shown as being included within the housing 102, the physiologic sensor(s) 170 may be external to the housing 102, yet still be implanted within or carried by the patient. Examples of physiologic sensors might include sensors that, for example, activity, temperature, sense respiration rate, pH of blood, ventricular gradient, activity, position/posture, minute ventilation (MV), and so forth. Examples of such physiologic sensors include accelerometers, temperature sensors, and/or the like.

A battery 172 provides operating power to all of the components in the ICM 100. The battery 172 is capable of operating at low current drains for long periods of time. The battery 172 also desirably has a predictable discharge characteristic so that elective replacement time can be detected. As one example, the housing 102 employs lithium/silver vanadium oxide batteries. The battery 172 may afford various periods of longevity (e.g., three years or more of device monitoring). In alternate embodiments, the battery 172 could be rechargeable.

The ICM 100 provides a simple to configure data storage option to enable physicians to prioritize data based on individual patient conditions, to capture significant events and reduce risk that unexpected events are missed. The ICM 100 may be programmable for pre- and post-trigger event storage. For example, the ICM 100 may be automatically activated to store 10-120 seconds of EGM data prior to an event of interest (e.g., an arrhythmia event) and/or to store 10-120 seconds of post EGM data. Optionally, the ICM 100 may afford patient triggered activation in which pre-event EGM data is stored, as well as post event EGM data (e.g., pre-event storage of 1-15 minutes and post-event storage of 1-15 minutes). Optionally, the ICM 100 may afford manual (patient triggered) or automatic activation for EGM data. Optionally, the ICM 100 may afford additional programming options (e.g., asystole duration, bradycardia rate, tachycardia rate, tachycardia cycle count). The amount of EGM data storage may vary based upon the size of the memory 160.

The ICM 100 may provide comprehensive safe diagnostic data reports including a summary of heart rate, in order to assist physicians in diagnosis and treatment of patient conditions. By way of example, reports may include episode diagnostics for auto trigger events, episode duration, episode count, episode date/time stamp and heart rate histograms. The ICM 100 may be configured to be relatively small (e.g., between 2-10 cc in volume) which may, among other things, reduce risk of infection during implant procedure, afford the use of a small incision, afford the use of a smaller subcutaneous pocket and the like. The small footprint may also reduce implant time and introduce less change in body image for patients.

Figure 2:
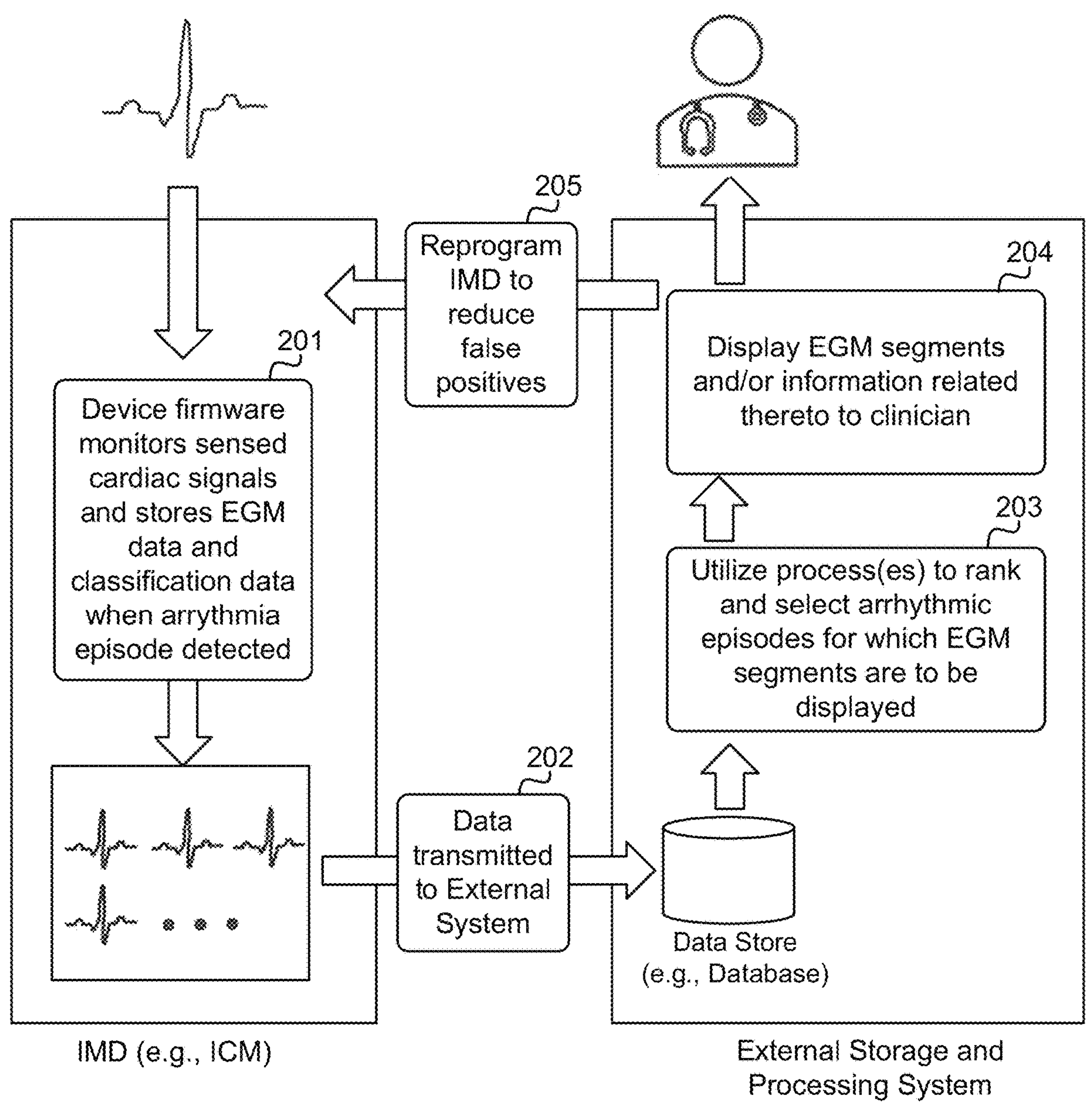
FIG. 2 shows a high-level overview of a system formed in accordance with certain embodiments of the present technology.

FIG. 2 shows a high-level overview of a system formed in accordance with certain embodiments of the present technology. At block 201, an EGM signal is analyzed by one or more arrhythmia detection algorithms in the IMD. When an arrhythmia is identified, one or more DCA data sets are recorded in connection with the arrhythmia episode, including device documented markers designating characteristics of interest within the EGM segment and/or identifying the nature of the arrhythmia. By way of example, one DCA data set may be recorded in connection with a single arrhythmia episode, where a single EGM segment may correspond to an initial portion of the arrhythmia episode (e.g., the first 30 seconds or one minute). Additionally, or alternatively, the single EGM segment may correspond to another portion of the arrhythmia episode, such as the end portion of the arrhythmia episode or a segment of the arrhythmia episode exhibiting a particular characteristic of interest. The patient may experience numerous arrhythmia episodes over a day, week, month or otherwise. The IMD continuously monitors the patient's heart and records one or more DCA data sets in connection with each separate arrhythmia episode, thereby forming a collection of DCA data sets associated with a corresponding collection of arrhythmia episodes over time. Each DCA data set for an arrhythmia episode can include, e.g., respective EGM data and respective classification data for the arrhythmia episode, and may also include marker data. Each DCA data set for an arrhythmia episode can also include a representative R-R interval and/or a representative HR for the episode, as well as duration data indicative of the duration of the episode.

Additionally or alternatively, the IMD may also identify normal sinus rhythms and record one or more device classified normal sinus (DCNS) data set, each of which can include an EGM data collected in response to a determination by an IMD that a sensed EGM signal is indicative of a normal sinus rhythm and one or more device documented markers related to one or more features of interest in the EGM segment that in whole or in part was utilized by the IMD in connection with the determination of the normal sinus rhythm. Such one or more DCNS data sets can be utilized as reference or baseline information for other analysis. The DCA data sets and the DCNS data sets can be referred to collectively as device classified (DC) data sets.

As shown at block 202 in FIG. 2, the DCA data sets and/or DCNS data sets (or more generally the DC data sets) that are stored within the memory (e.g., 160) of the ICM (or other type of IMD) are transmitted to an external storage and processing system. At various points in time, the IMD establishes a communication session with an external device, during which the opportunity arises to upload the recorded DC data sets from the IMD to the external device (e.g., 154), for subsequent transmission to a remote server, clinician workstation or other computing device. At block 202, the collection of DC data sets are wirelessly transmitted from the IMD to a local external device (e.g., 154) and/or a remote server. For example, the IMD can wireless transmit DC data sets to a bedside monitor installed in a patient's home, and the bedside monitor can in-turn transmit the DC data sets to over a network (e.g., the Internet) to a remote monitoring service, medical network and/or the like. In such a case, the bedside monitor acts as an intermediate communication device between the IMD and a remote monitoring service, medical network and/or the like. Other types of external devices 154 can be used as an intermediate communication device, in place of the bedside monitor, such as smartphone, tablet device, laptop computer, smartwatch and/or the like, which can be coupled over a network (e.g., the Internet) to a remote monitoring service, medical network and the like.

There are three types of transmissions of DC data sets that may occur at block 202, wherein each of the types of transmission involve transmitting all of the DC data sets that were stored by the IMD since the last transmission. The three types of transmissions of DC data sets include: (1) schedule transmissions, (2) alert transmissions, and (3) patient-initiated transmissions. The scheduled transmissions are periodic transmissions that automatically initiated at the end of a programmable period, e.g., at the end of each day, week, or month, but not limited thereto. The alert transmissions are automatically initiated when the IMD detects that a configurable alert condition has been met, e.g., an AF episode lasting longer than 6 hours occurred in a single day. The patient-initiated transmissions are initiated in response to a patient using an external device, such as a bedside monitor or smartphone, to initiate the transmission. A patient may initiate such transmissions, e.g., in response to experiencing symptoms of an arrhythmia. Each transmission of the DC data sets can include EGM data and classification data for all new EGM segments and corresponding episode metadata, such as, episode duration and arrhythmia-specific representative rate. Each EGM segment typically includes approximately 30 sec pre-detection and 2 min post-detection for AF, with 30 sec pre-detection and 30 sec post-detection for tachycardia, bradycardia, and pause. In accordance with certain embodiments, once DC data sets have been transmitted to an external device or system, the portion of the memory 160 that had been used to store the DC data sets (that were uploaded to the external device or system) can be erased and/or overwritten with new DC data sets.

At block 203 in FIG. 2, the external device and/or remote server, which can collectively or individually be referred to as an external system, utilize one or more processes, as described herein, to rank (aka prioritize) arrhythmic episodes and select, based on results of the ranking, arrhythmic episodes for which corresponding EGM segments are to be displayed to a clinician.

At block 204 in FIG. 2, EGM segments and/or information related to the EGM segments for one or more DCA data sets are presented, and more specifically displayed, to a clinician.

At block 205 in FIG. 2, which is optional, one or more sensing parameters and/or arrhythmia discrimination parameters of the IMD are reprogrammed to reduce the probability of false positive detections of one or more types of arrhythmias. This can include, e.g., reducing a sensing threshold to reduce R-wave undersensing, increasing a sensing threshold to reduce P-wave oversensing and/or T-wave oversensing. Additionally, or alternatively, this can include adjusting morphology matching templates, arrhythmia discrimination algorithms, and/or the like.

Figure 3:
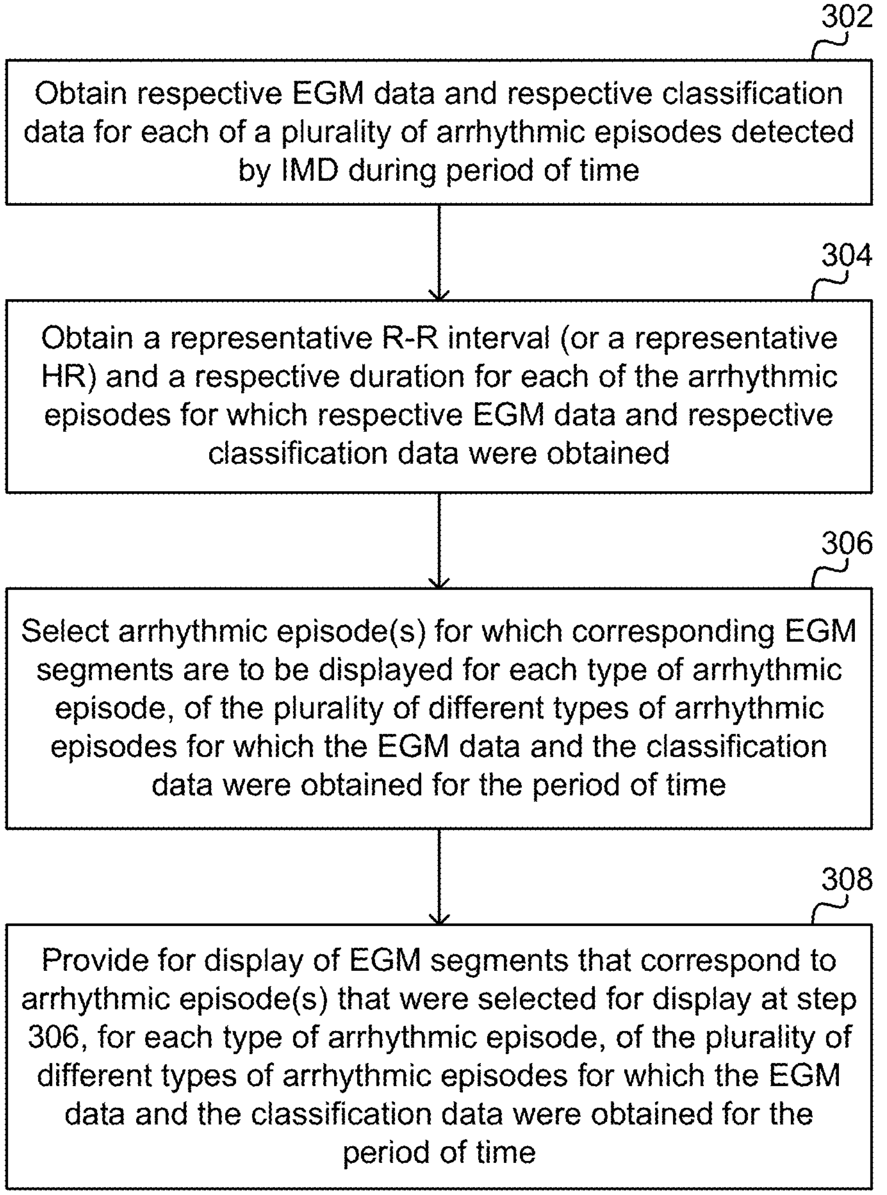
FIG. 3 is a high level flow diagram that is used to summarize methods according to certain embodiments of the present technology.

The high level flow diagram of FIG. 3 will now be used to summarize certain methods of the present technology that can be used for reducing a burden associated with analyzing EGM segments obtained from an IMD (e.g., ICM 102) that is configured to monitor for arrhythmic episodes.

Referring to FIG. 3, step 302 involves obtaining respective EGM data and respective classification data for each arrhythmic episode of a plurality of arrhythmic episodes that were detected by the IMD during a period of time. The respective EGM data is indicative of an EGM segment corresponding to the arrhythmic episode, and can be used to display the EGM segment to a clinician. The respective classification data specifies a type of the arrhythmic episode, such as, but not limited to, bradycardia, tachycardia, cardiac pause, and AF. As mentioned above, such EGM data can include temporal (e.g., morphological) information and frequency information about the EGM segment, which information enables the EGM segment to be reproduced for display to medical personal, and enables the EGM segment to be analyzed, e.g., for the purpose of ranking the arrhythmia episode corresponding to the EGM segment, determining whether the arrhythmia detection was a true positive or a false positive detection, determining whether the arrhythmia episode should be reclassified is being a different type of arrhythmia than originally classified, and/or the like. The respective classification data specifies a type of the arrhythmic episode. The EGM data and the classification data obtained at step 302 can be obtained directly from an IMD (e.g., 102) that stored such data in its memory (e.g., 160). Alternatively, the EGM data and the classification data obtained at step 302 can be obtained from an external device (154) that had already obtained such data from an IMD. The data obtained at step 302 can also include marker data, examples of which were discussed above, and other types of metadata. Explained another way, the data obtained at step 302 can include multiple device classified arrhythmia (DCA) data sets. Additionally, one or more device classified normal sinus (DCNS) data sets can also be obtained as part of step 302, or more generally, device classified (DC) data sets can be obtained at step 302. In accordance with certain embodiments, step 302 is performed by a non-implantable system (such as a programmer, remote monitor, or bedside monitor) that wirelessly communicates with the IMD, or is performed by a non-implanted system (e.g., a remote server) that communicates with another non-implanted system (e.g., such as a programmer, remote monitor, or bedside monitor) that wirelessly communicate with the IMD. In accordance with certain embodiments, step 302 is performed by an external storage and processing system that is used to analyze DCA data sets obtained from numerous IMDs that are implanted in numerous patients. Other variations are also possible and within the scope of the embodiments described herein.

It is noted that the terms "obtain" and "obtaining", as used in connection with data, signals, information and the like, includes at least one of i) accessing memory of an IMD, ICM, external device or remote server where the data, signals, information, etc. are stored, ii) receiving the data, signals, information, etc. over a wireless communications link between the ICM or IMD and a local external device, iii) receiving the data, signals, information, etc. at a remote server over a network connection and/or iv) sensing signals (e.g., CA signals, impedance signals, etc.) between a combination of electrodes provide on or coupled to the ICM or IMD. An obtaining operation, when from the perspective of an ICM or IMD, may include sensing new signals in real time, and/or accessing memory to read stored data, signals, information, etc. from memory within the ICM or IMD. The obtaining operation, when from the perspective of a local external device, includes receiving the data, signals, information, etc. at a transceiver of the local external device where the data, signals, information, etc. are transmitted from an ICM and/or a remote server. The obtaining operation may be from the perspective of a remote server, such as when receiving the data, signals, information, etc. at a network interface from a local external device and/or directly from an ICM. The remote server may also obtain the data, signals, information, etc. from local memory and/or from other memory, such as within a cloud storage environment and/or from the memory of a workstation or clinician external programmer.

Still referring to FIG. 3, step 304 involves obtaining a representative R-R interval, or a representative heart rate (HR), for each of the arrhythmic episodes for which respective EGM data and respective classification data were obtained. Step 304 can also involve obtaining a respective duration for each of the arrhythmic episodes for which respective EGM data and respective classification data were obtained. In accordance with certain embodiments, a manner for determining the representative R-R interval or the representative HR for an arrhythmic episode depends on the type of the arrhythmic episode, such that for at least two of the different types of arrhythmic episodes the manners for determining the representative R-R interval or the representative HR differ from one another. Specific manners for determining a representative R-R interval or a representative HR for each of a plurality of different types of arrhythmic episodes, are described below.

In accordance with certain embodiments, step 304 is performed by the same non-implanted system that performs step 302. Indeed, in certain embodiments, steps 302 and 304 are performed at the same time. More specifically, the IMD may maintain an episode diagnostic log that records for each detected arrhythmic episode, the type of arrhythmic episode (e.g., bradycardia, tachycardia, cardiac pause, or AF), the representative R-R interval or the representative HR as determined by the IMD, and a duration of the arrhythmic episode. More specifically, in certain embodiments, whenever the IMD detects an arrhythmic episode, the IMD saves (aka records) two values for the episode, a representative R-R interval (or a representative HR) for the episode, and a duration of the episode. Various different techniques which are known in the art may be used by the IMD to detect and classify various different types of cardiac arrhythmias, as well as to determine durations of the various different types of cardiac arrhythmias. At the same time that the EGM data is obtained by the non-implanted system, directly or indirectly (e.g., with a programmer or bedside monitor acting as an intermediary) from the IMD, the diagnostic log is also obtained by the non-implanted system, and the non-implanted system (e.g., a server) links the EGM data for each episode to its corresponding representative R-R interval (and/or the representative HR) and corresponding episode duration.

In certain embodiments, where the arrhythmic episode is a bradycardia type of arrhythmic episode, the representative R-R interval (or the representative HR) is a longest R-R interval (or equivalently, a slowest HR) during the bradycardia episode. Where the arrhythmic episode is a tachycardia type of arrhythmic episode, the representative R-R interval (or the representative HR) is a shortest R-R interval (or equivalently a fastest HR) during the tachycardia episode. Where the arrhythmic episode is an AF type of arrhythmic episode, the representative R-R interval (or the representative HR) is a mean (aka average) R-R interval or (equivalently a mean HR) during the AF episode. Where the arrhythmic episode is a cardiac pause type of arrhythmic episode, the representative R-R interval (or the representative HR) is a longest R-R interval during the cardiac pause episode or the representative HR that is fastest.

Referring again to FIG. 3, step 306 involves selecting one or more arrhythmic episodes for which corresponding EGM segments are to be displayed for each type of arrhythmic episode, of the plurality of different types of arrhythmic episodes for which the EGM data and the classification data were obtained for the period of time. In accordance with specific embodiments, the selecting that is performed at step 306 is based on the representative R-R intervals or the representative HRs that are determined for the plurality of arrhythmic episodes.

In accordance with certain embodiments, for the bradycardia type arrhythmic episodes, the EGM segments that are selected for display include the EGM segment having a representative R-R interval that is shortest (or equivalently, a representative HR that is fastest). For the tachycardia type arrhythmic episodes, the EGM segments that are selected for display include the EGM segment having a representative R-R interval that is shortest (or equivalently, a representative HR that is fastest). For the cardiac pause type episodes, the EGM segments that are selected for display include the EGM segment having a representative R-R interval that is shortest (or equivalently, a representative HR that is fastest). For the AF type arrhythmic episodes, the EGM segments that are selected for display include the EGM segment having a representative R-R interval that is shortest (or equivalently, a representative HR that is fastest). It is noted that a fastest HR can also be referred to as a maximum HR, and a slowest HR can also be referred to as a minimum HR.

Step 306 can also involve selecting, for each type of arrhythmic episode, the episode having the longest duration, or the two episodes having the longest durations (i.e., the first longest duration and the second longest duration).

Step 308 involves providing for display of the EGM segments that correspond to the one or more arrhythmic episodes that were selected for display, for each type of the arrhythmic episodes, of the plurality of different types of arrhythmic episodes for which the EGM data and the classification data were obtained for the period of time. The result of step 308 is that one or more EGM segments for each type of arrhythmic episode are available for display to a clinician, and eventually, are caused to be displayed to the clinician.

Using an embodiment described above with reference to the high level flow diagram of FIG. 3, for each bradycardia episode (of a plurality of bradycardia episodes that were detected by the IMD during a period of time, e.g., 1 day), the system identifies a longest R-R interval that occurred during the bradycardia episode, and uses the longest R-R interval as the representative R-R interval for the bradycardia episode, as was described above. For example, assume the IMD detected ten bradycardia episodes during a period of time (e.g., during a 24 hour period), and that the longest R-R interval for each the ten bradycardia episodes are as shown in the below table. The representative HR for each bradycardia episode, which is shown in the right most column of the below table, was calculated using the equation: Rep HR=60/longest R-R interval (e.g., 60/1.5=40.0).

| Brady Episode No. | Episode Duration (in seconds) | Longest R-R interval within Episode (in seconds) | Representative HR for Brady Episode (in beats per minute) |
|---|---|---|---|
| 1 | 60 | 1.50 | 40.0 |
| 2 | 120 | 1.82 | 33.0 |
| 3 | 200 | 1.72 | 34.9 |
| 4 | 110 | 2.5 | 24.0 |
| 5 | 320 | 1.65 | 36.4 |
| 6 | 235 | 1.77 | 33.9 |
| 7 | 340 | 1.52 | 39.5 |
| 8 | 77 | 1.69 | 35.5 |
| 9 | 133 | 1.66 | 36.1 |
| 10 | 205 | 1.55 | 38.7 |

As can be appreciated from the above table: for the bradycardia episode 1, the representative R-R interval is the 1.50 sec longest R-R interval (or equivalently, the fastest HR during the episode is 40.0 bpm) that occurred during the episode; for the bradycardia episode 2, the representative the representative R-R interval is the 1.82 sec longest R-R interval (or equivalently, the fastest HR during the episode is 33.0 bpm) that occurred during the episode; . . . and for the bradycardia episode 10, the representative R-R interval is the 1.55 sec longest R-R interval (or equivalently, the fastest HR during the episode is 38.7 bpm) that occurred during the episode.

In accordance with certain embodiments, the system selects to display (to a clinician) the bradycardia episode having the longest duration (or the bradycardia episodes having the 1st and 2nd longest durations), as well as the bradycardia episode having the shortest representative R-R interval (which is the equivalent to saying that the system selects the bradycardia episode having the fastest representative HR). Selecting the bradycardia episode having the shortest representative R-R interval (and thus, the fastest representative HR) is counterintuitive, because such an episode would likely not be the most symptomatic episode. However, the bradycardia episode having the shortest representative R-R interval (and thus, the fastest representative HR) has a high probability of corresponding to a true positive bradycardia detection, i.e., there is a high probability that this bradycardia episode (for which an EGM segment is to be displayed) is an actual bradycardia episode. By contrast, there is a high probability that the longest R-R interval in the bradycardia episode having the slowest representative HR resulted from R-wave undersensing, and thus, that the bradycardia episode including the longest R-R interval was a false positive detection of a bradycardia episode. For example, looking at the above table, the bradycardia episode 4 is shown as having a longest R-R interval of 2.5 sec, and a representative HR of 24 bpm. The system does not select the bradycardia episode 4 for display, because there is a high probability that the 2.5 sec longest R-R interval (which is the representative R-R interval for that episode) that was detected during that episode occurred due to R-wave undersensing. Accordingly, using the embodiment just described above, for bradycardia, the system will select for display the bradycardia episode having the fastest representative HR (or equivalently, the shortest representative HR), which is counterintuitive, as well as the bradycardia episodes having the first and second longest durations, so that a total of three bradycardia episodes for the period of time are displayed, rather than displaying all of the bradycardia episodes that occurred during the period of time, which may be numerous.

Selecting (for display) the cardiac pause episode having the shortest representative R-R interval (and thus, the fastest representative HR) is also counterintuitive, because such an episode would likely not be the most symptomatic episode. However, the cardiac pause episode having the shortest representative R-R interval (and thus, the fastest representative HR) has a high probability of corresponding to a true positive cardiac pause detection, i.e., there is a high probability that this cardiac pause episode (for which an EGM segment is to be displayed) is an actual cardiac pause episode. By contrast, there is a high probability that the longest R-R interval in a cardiac pause episode having the slowest representative HR resulted from R-wave undersensing.

In accordance with certain embodiments, if three or fewer episodes of a type or arrhythmia were detected for the period of time (e.g., one day), then the EGM segments for all of those episodes are selected for review.

In accordance with certain embodiments, if a single episode for a type of arrhythmia satisfies two criteria for being selected, e.g., if there were three episodes of VF detected during the period of time, and one of the episodes had both the fastest representative HR and the longest duration, then only two episodes of that type of arrhythmia (rather than three) may be selected for display.

Where the EGM data and respective classification data is initially obtained by an ICM, the ICM may be used for diagnostic purposes, e.g., to identify whether a patient experiences arrhythmic episodes, and if so, what types of arrhythmic episodes. More specifically, the ICM can collect EGM data and respective classification data for a period of time, e.g., a month, and such data can then be uploaded to a non-implanted system of a patient care network. Conventionally, a clinician would need to review all of the EGM segments to confirm or reject the arrhythmia classifications determined by the ICM, and based thereon, the clinician can determine whether the patient should have a pacemaker implanted, be prescribed certain medication, have a certain medical procedure performed, and/or the like. However, as mentioned above, it is quite burdensome for a clinician to review all EGM segments that have been uploaded from an ICM or other type of IMD. Embodiments of the present technology, including those just summarized above, can be used to reduce the unnecessary EGM review burden imposed on ICM customers, while minimizing any delay-to-diagnosis. For example, such embodiments can be used to reduce the number of EGM segments that a clinician needs to review per time period (e.g., per day) for each type of arrhythmic episode from potentially dozens per day, to just three per day, while still enabling the clinician to identify a true positive arrhythmia detection on the first day such data was collected by an ICM in over 98% of patients for which such embodiments were tested. In other words, by reducing the number of EGM segments that need to be manually reviewed by a clinician, per type of arrhythmia, to at most three EGM segments per day using an embodiment summarized above with reference to FIG. 3, for less than 2% of patients there was a delay of at least one day in the patients being diagnosed as having a true positive arrhythmic episode.

In the embodiments summarized above with reference to FIG. 3, a few rules were used to essentially rank and decide which EGM segments should be selected for display. In further embodiments, summarized below with reference to the high level flow diagram of FIG. 4, alternative and/or additional rules can be used for the ranking and selecting which EGM segments should be displayed.

Figure 4:
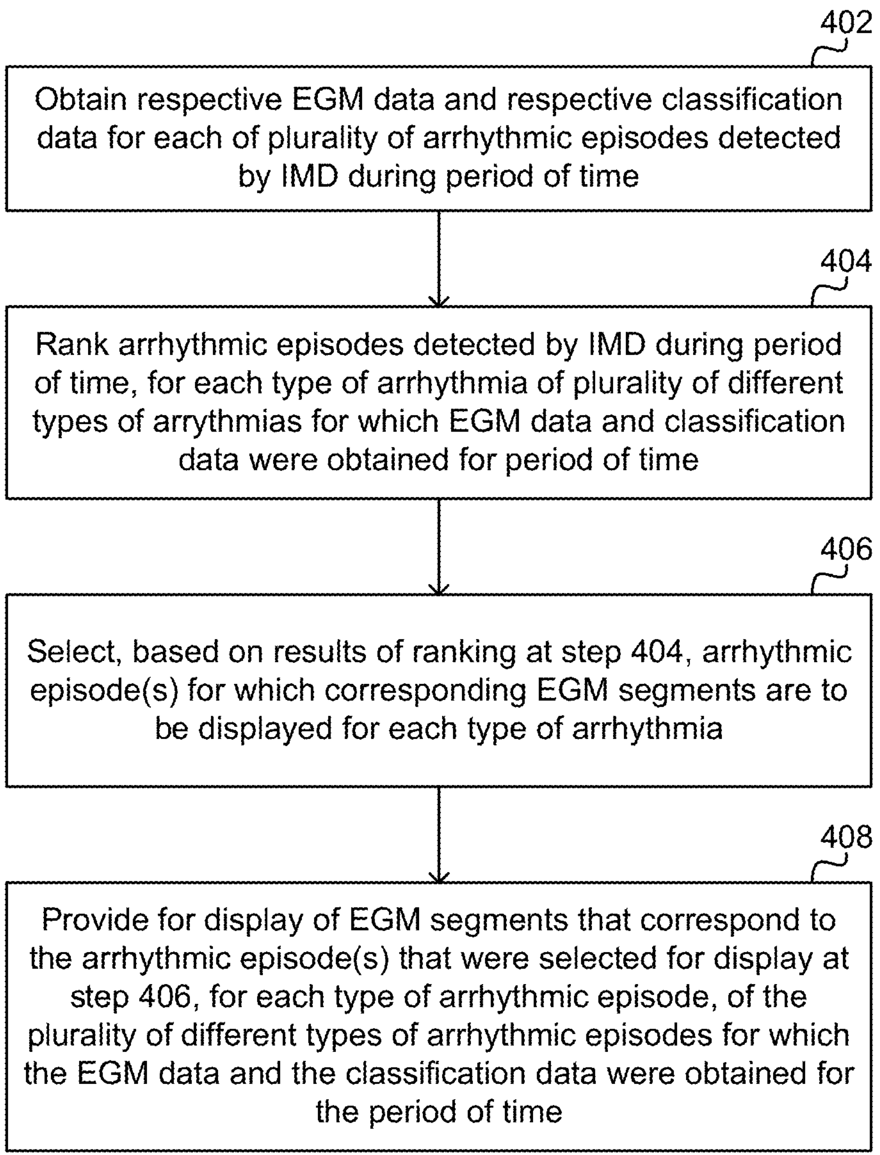
FIG. 4 a high level flow diagram that is used to summarize methods according to other embodiments of the present technology.

Referring to FIG. 4, step 402 involves obtaining respective EGM data and respective classification data for each arrhythmic episode of a plurality of arrhythmic episodes that were detected by an IMD during a period of time, wherein the respective EGM data is indicative of an EGM segment corresponding to the arrhythmic episode, and wherein the respective classification data specifies a type of the arrhythmic episode. Step 402 is the same as step 302 described above, and thus additional details of step 402 can be appreciated from the above discussion of step 302.

Step 404 involves ranking the arrhythmic episodes for each type of arrhythmic episode, of the plurality of different types of arrhythmic episodes for which the EGM data and the classification data were obtained for the period of time, wherein the ranking that is performed at step 404 is performed using rules. More specifically, based on various different characteristics of arrhythmic episodes of the same type (e.g., bradycardia), each arrhythmic episode can be assigned a ranking score that enables arrhythmic episodes of the same type (e.g., bradycardia) to be compared to one another. The ranking that is performed at step 404, is separately performed for each type of arrhythmia of a plurality of different types of arrhythmias for which the EGM data and the classification data were obtained. For example, if the data obtained at step 402 was for a plurality of AF episodes, and a plurality of VT episodes, then the AF episodes will be ranked, and the VT episodes will be separately ranked.

To enable the rankings, each of the arrhythmic episodes can be characterized, and then based on the characterizations of the arrhythmic episodes, the arrhythmic episodes can be ranked from highest priority (aka highest ranking) to a lowest priority (aka lowest ranking). Characterizations for an arrhythmic episode can include, but are not limited to, a representative R-R interval and/or HR of the episode, a duration of the episode, a time of day, a frequency of the type of episode, and/or EGM signal amplitude and its variation within the episode. At least some of the aforementioned characterizations, such as, but not limited to, a duration and time of day of the episode, may have been included in the metadata that was obtained from an IMD. Other characterizations, such as, but not limited to, a representative R-R interval and/or HR of the episode, may be determined by an external system, or by the IMD itself. Other types of characterizations that can be determined for an arrhythmic episode, and used to rank the episode, include a similarity to an episode that has been adjudicated by a clinician as being an actual arrhythmic episode. Further examples of characterizations include a degree of noise interruption, and a degree of R-wave undersensing, a degree of P-wave oversensing, and/or a degree of T-wave oversensing. Other physiological conditions during the episode, such as activity, posture, heart sound, heart rate variability, respiratory pattern, and/or the like, can also be used to characterize and rank an arrhythmic episode. Additional details of step 404, according to certain embodiments of the present technology, are provided below, following an initial discussion of the remaining steps shown in FIG. 4.

Still referring to FIG. 4, step 406 involves selecting, based on results of the ranking, one or more arrhythmic episodes for which corresponding EGM segments are to be displayed for each type of arrhythmic episode, of the plurality of different types of arrhythmic episodes (e.g., bradycardia, cardiac pause, VT, VF, etc.) for which the EGM data and the classification data were obtained for the period of time. For an example, for each type of arrhythmic episode, a specified number (e.g., three) of the episodes having the highest ranking scores can be selected for display at step 406. In accordance with certain embodiments, up to three EGM segments of each type of arrhythmia is selected for display. This is because it has been shown that limiting the display of EGM segments to three per period, per type of arrhythmia, resulted in a substantially optimal balance of maximal EGM burden reduction with minimal true positive (TP) day reduction.

Step 408 involves providing for display of EGM segments that correspond to the one or more arrhythmic episodes that were selected for display, for each type of arrhythmic episode, of the plurality of different types of arrhythmic episodes for which the EGM data and the classification data were obtained for the period of time. The result of step 408 is that one or more EGM segments for each type of arrhythmic episode are made available for display to a clinician, and eventually are displayed to the clinician.

Various rules that can be used for performing the rankings at step 404 are described below. Each such rule can be used to produce a respective ranking score, and where multiple rules are used to produce multiple ranking scores for each arrhythmic episode, the ranking scores can be combined to produce an overall score that can then be used, at step 406, for selecting which EGM segments are to be displayed. For example, multiple scores can be averaged using simple averaging, wherein each score is equally weighted. Alternatively, weighted averaging can be used such that some rules or characteristics are weighted more heavily than others. Instead of using averaging to combine multiple ranking scores, ranking scores can instead by summed, using a simple summation, or a weighted summation. Other variations are also possible and within the scope of the embodiments described herein.

Various different rules, or combinations thereof, can be used to produce the ranking score for each arrhythmic episode. In accordance with certain embodiments, the ranking score for each arrhythmic episode is based on one or more of the following: a degree of noise in the EGM segment that corresponds to the arrhythmic episode; a proximity of the arrhythmic episode to one or more noise interruptions; an extent of R-wave undersensing during the arrhythmic episode; an extent of at least one of P-wave or T-wave oversensing during the arrhythmic episode; an extent of similarity between the EGM segment that corresponds to the arrhythmic episode that was classified as a specific type of arrhythmic episode, and a previously adjudicated EGM segment determined to actually correspond to the specific type of arrhythmic episode; an extent of similarity between the EGM segment that corresponds to the arrhythmic episode that was classified as a specific type of arrhythmic episode, and a previously adjudicated EGM segment determined to not actually correspond to the specific type of arrhythmic episode; a time of day when the arrhythmic episode occurred; and/or a level of variation in an amplitude of the EGM segment that corresponds to the arrhythmic episode.

For still another example, activity and/or posture information, obtained using an accelerometer within the IMD, can also be used for ranking arrhythmic episodes. For example, during certain types of arrhythmic episodes experienced by a patient, an accelerometer would be expected to detect certain types of motion and/or posture. For instance, during a cardia pause, a patient loses consciousness, typically falls to the ground, and all activity for the patient ceases. Therefore, an accelerometer would be able to detect that activity of the patient has ceased, or that the position of the individual has gone from standing to laying down during the interval associated with the syncope. Physical actions experienced by the patient may include the absence of activity of the patient, variation in activity of the patient, increase in sudden but transient activity associated with fall to the ground, activity of the patient decreasing below a threshold level, a patient moving from a standing to a laying down position, a patient moving from a sitting to a laying down position, a patient moving from a sitting upright to slumped position, a patient moving from sitting upright to laying on a side, etc. To this end, a likelihood that a patient actually experienced a cardia pause, i.e., that the detection of the cardia pause episode was a true positive, can be determined at least in part based on one or more signals generated by an accelerometer. Where one or more signals produced by an accelerometer increases the confidence level that a specific type of arrhythmic that was detected, such information can be used to increase a ranking of the arrhythmic episode. Conversely, where one or more signals produced by an accelerometer reduces the confidence level that a specific type of arrhythmic that was detected, such information can be used to reduce a ranking of the arrhythmic episode.

Various heart rate metrics can be used as a representative R-R interval and/or HR to characterize and rank an arrhythmic episode, such as the mean, median, standard deviation (SD), coefficient of variation (SD divided by mean), fastest beat, or slowest beat across all beats during the episode. For example, AF or tachycardia episodes with a higher mean heart rate may have higher priority (aka higher ranking) than other of the same arrhythmia type, whereas bradycardia episodes with lower minimum heart rate may have higher priority than other bradycardia episodes. Specific types of representative R-R intervals and/or HRs that can be used for specific types of arrhythmic episodes, according to certain embodiments of the present technology, were described above with reference to step 304, and thus, need not be repeated.

A degree of noise interruption and incidence of sensing issues (i.e., undersensing or oversensing) can correlate to the probability of a false detection. Noise interruption can be quantified by the percent of beats associated with (e.g., overlapping with, and/or within a specified amount of time of) a noise interrupt. Similarly, abnormal sensing can be quantified by the percent of inappropriately sensed beats (such as R-wave undersensing, P-wave oversensing, and T-wave oversensing). Episodes with a higher degree of noise interruption and/or sensing issue are less likely to be true episode, and thus will have a lower priority (aka lower ranking). Similarly, arrhythmic episodes that occur close in time (i.e., close in temporal proximity) to one or more noise interruptions are less likely to be a true episode than episodes that do not occur close in time to one or more noise interruptions. Therefore, episodes that occur close in time to one or more noise interruptions may be ranked lower than episodes that do not occur close in time to any noise interruptions, as also mentioned above.

Time of day is useful to identify a clinically actionable bradycardia episode. At nighttime, heart rates typically slow down and may trigger bradycardia episode detections. However, bradycardia episodes during sleep may not be as important as bradycardia episodes during the day. Thus, bradycardia episodes detected during the day may have higher priority than bradycardia episodes detected at night. Arrhythmia episodes can have diurnal variation. For example, publications have demonstrated that more AF episodes typically occur during the afternoon and evening, than in the morning. Therefore, AF episodes detected during the afternoon and evening hours can have a higher priority (aka higher rank) than AF episodes that occur during morning hours.

Event frequency and proximity also matters. Multiple episodes of the same type of arrhythmia that are detected within a short amount of time may result from a same underlying mechanism. For example, an ICM may enter and exit AF detection several times during a long-lasting AF event, resulting in EGM data for multiple AF episodes being saved within a short period of time, even though in actuality there was really just one long-lasting AF episode. For another example, an ICM may trigger several false cardiac pause detections due to repeated R-wave undersensing during activity, or when the patient assumes a certain posture. Therefore, if one of a plurality of cardia pause episodes that occurred close in time is ranked high, the other episode(s) close in time may have a lower priority.

The amplitude and degree of variation in EGM amplitude during a detected arrhythmic episode provide insight into a likelihood of the detected episode being true or false detection. EGM episodes with more signal amplitude variation and/or low signal amplitude (e.g., <0.2 mV) are more likely to be false due to a sensing issue. Therefore, arrhythmic episodes that have a high amplitude variation, or a low overall amplitude, may have a lower priority (aka rank) than other episodes with less amplitude variation and/or higher overall signal amplitude.

Similarity of an EGM segment of a detected arrhythmic episode to the EGM segment(s) of one or more other episodes that has/have already been adjudicated as corresponding to an actual (i.e., true positive) arrhythmia can be used to characterize and rank the arrhythmic episode. Example techniques for categorizing arrhythmic episodes based on similarity are described in U.S. Patent Application No. 63/119,099, filed Nov. 30, 2020, which is incorporated herein by reference. For example, the morphology of an EGM segment of a detected AF episode can be compared to the morphology of one or more EGM segments that are known to correspond to actual AF episodes for that patient, and the greater the level of similarity the higher that episode may be ranked. In certain embodiments, newly detected episodes can be compared to previously adjudicated episodes for similarity, and episodes classified to a true positive group will have higher priority than the episodes classified to a false positive group.

Other physiological information, such as activity, posture, heart sound, heart rate variability, electrode impedance, and respiration pattern information during the episode can also be utilized in prioritization (aka ranking). This information can be used either directly or in combination with other criteria described above. For example, if electrode impedance is outside of the common physiological range during an episode, it is more likely a false positive detection and can have a lower priority. In another example, an episode associated with excessive patient activity and large EGM signal amplitude variation may be falsely detected, and can have a lower priority. Similarly, an episode triggered during a certain posture and associated with a decreased signal amplitude may also have been falsely detected, and can have a lower priority.

Where various different characterizations of arrhythmic episodes are used to rank arrhythmic episodes of the same type (e.g., to rank twenty AF episodes in order from highest priority to lowest priority), certain characterizations can be weighted greater than others when ranking the arrhythmic episodes. For example, where a specific characterization of an arrhythmic episode provides a high probability that the episode was a false positive detection, that characterization can be give a great amount of weight. Further, it is noted that the way arrhythmic episodes are ranked can differ for different types of arrhythmias. For examples, rules and weightings that are used to rank AF episodes may differ from rules that are used to rank VT episodes.

In accordance with certain embodiments, arrhythmic episodes with a longer duration have a higher priority than other episodes of the same arrhythmia type. For example, an AF episode that lasts for 20 minutes can be ranked higher than an AF episode that lasts for 10 minutes.

Referring above to FIGS. 3 and 4, in certain embodiments the EGM data and respective classification data obtained at steps 302 and 402 are stored in cloud storage (or some other remote storage), and the selecting performed at steps 306 and 406 is performed by selecting such data from the data stored in the cloud storage. Such selecting can be performed, in certain embodiments, by tagging the data that is to be displayed, such that when a clinician logs into a patient care network, the selected episodes will be displayed to the clinician for the clinician to review, optionally along with associated alerts. It may also be possible for the clinician to turn off selection criteria such that all EGM data and respective classification data is displayed to the clinician via the patient care network. Other variations are also possible and within the scope of the embodiments described herein.

Example External Device

Figure 5:
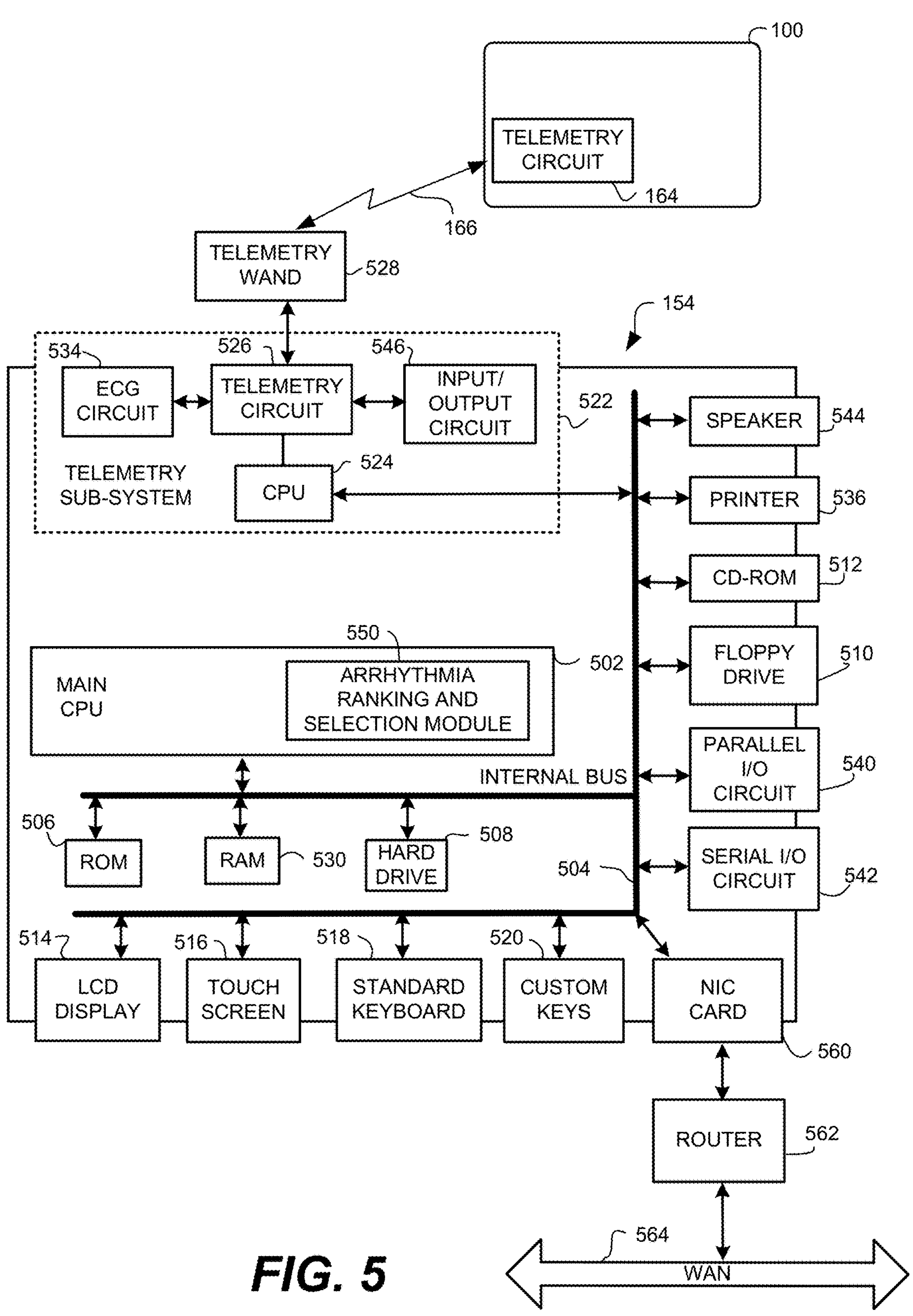
FIG. 5 shows a block diagram of one embodiment of an external device for use in communicating with and/or programming the ICM introduced in FIG. 1, or some of the type of implantable medical device (IMD), and which can be used to implement certain embodiments of the present technology.

FIG. 5 illustrates example components of an example external device 154 for use in communicating with and/or programming the ICM 100, or other type of IMD 100. In certain embodiment, the external device 154 can be used to analyze EGM segments obtained and stored by the IMD 100. More generally, the external device 154 may permit a physician or other authorized user to program the operation of the IMD 100 and to retrieve and display information received from the IMD 100 such as EGM data and device diagnostic data. Further, the external device 154 may be capable of causing the IMD to perform functions necessary to complete certain algorithms of the present invention. Depending upon the specific programming of the programmer, external device 154 may also be capable of processing and analyzing data received from the IMD 100. Additionally, the external device 154 is capable of accepting the various user inputs that are accepted in accordance with embodiments of the present invention described above.

Now, considering the components of the external device 154 by reference to FIG. 5, operations of the external device 154 can be controlled by a CPU 502, which may be a generally programmable microprocessor or microcontroller or may be a dedicated processing device such as an Application Specific Integrated Circuit (ASIC) or the like. Software instructions to be performed by the CPU can be accessed via an internal bus 504 from a Read Only Memory (ROM) 506 and Random Access Memory (RAM) 530. Additional software may be accessed from a hard drive 508, floppy drive 510, and CD ROM drive 512, or other suitable permanent mass storage device. Depending upon the specific implementation, a Basic Input Output System (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 514 or another suitable computer display device. To this end, the CPU may, for example, display a menu of specific programming parameters of the IMD 100 to be programmed or may display a menu of types of diagnostic data to be retrieved and displayed. In response thereto, the physician enters various commands via either a touch screen 516 overlaid on LCD display 514 or through a standard keyboard 518 supplemented by additional custom keys 520, such as an emergency VVI (EVVI) key. The EVVI key sets the IMD 100 to a safe VVI mode with high pacing outputs. This ensures life-sustaining pacing operation in nearly all situations but by no means is it desirable to leave cardiac stimulation device 100 in the EVVI mode at all times.

Typically, the physician initially controls the external device 154 to retrieve data stored within the IMD and to also retrieve ECG data from ECG leads coupled to the patient's myocardium. To this end, CPU 502 transmits appropriate signals to a telemetry circuit 522, which provides components for directly interfacing with IMD 100. The telemetry subsystem 522 can include its own separate CPU 524 for coordinating the operations of the telemetry subsystem 522. The main CPU 502 of the external device 154 communicates with telemetry subsystem CPU 524 via internal bus 504. The telemetry subsystem 522 additionally includes a telemetry circuit 526 connected to a telemetry wand 528, which cooperate to receive and transmit signals electromagnetically from telemetry circuit 164 of the IMD 100. The telemetry wand 528 is placed over the chest of the patient near the IMD 100 to permit reliable transmission of data, over communication link 166, between the telemetry wand and the IMD 100. Typically, at the beginning of the programming session, the external programming device controls the IMD 100 via appropriate signals generated by telemetry wand 528 to output all previously recorded patient and device diagnostic information. Patient diagnostic information includes, for example, measured physiological variables data, recorded EGM data and statistical patient data such as the percentage of paced versus sensed heartbeats. Device diagnostic data includes, for example, information representative of the operation of the IMD 100 such as lead impedances, battery voltages, battery Recommended Replacement Time (RRT) information and the like. Data retrieved from the IMD 100 is stored by the external device 154 either within a Random Access Memory (RAM) 530, a hard drive 508, within a floppy diskette placed within a floppy drive 510, etc. Additionally, or in the alternative, data may be permanently or semi-permanently stored within a Compact Disk (CD) or other digital media disk, if the overall system is configured with a drive for recording data onto digital media disks, such as a Write Once Read Many (WORM) drive.

Patient and device diagnostic data stored within the IMD 100 can be transferred to the external device 154. Further, the IMD 100 can be instructed to perform an electrode algorithms of the present invention, details of which are provided above.

The external device 154 can also include a Network Interface Card ("NIC") 560 to permit transmission of data to and from other computer systems via a router 562 and Wide Area Network ("WAN") 564. Alternatively, the external device 154 might include a modem for communication via the Public Switched Telephone Network (PSTN). Depending upon the implementation, the modem may be connected directly to internal bus 504 and may be connected to the internal bus via either a parallel port 540 or a serial port 542. Data transmitted from other computer systems may include, for example, data regarding medication prescribed, administered, or sold to the patient.

The CPU 502 can include an arrhythmia ranking and selection module 550 that can control the performance of the steps described above with reference to FIGS. 1A-4, or subsets thereof, and/or can instruct the IMD 100 to perform certain such steps. More generally, the arrhythmia ranking and selection module 550 can be implemented using hardware, software, firmware, or any combination thereof. It is also noted that the arrhythmia ranking and selection module 550, or at least a portion thereof, can be implemented by a remote server that obtains data from the IMD 100. Such a remote server can include one or more processors and a data store (e.g., memory), but is not limited thereto.

The external device 154 receives data from the IMD 100, including parameters representative of the current programming state of the IMD 100. The external device 154 can also receive EGMs, samples thereof, and/or date indicative thereof from the IMD 100. Under the control of the physician, external device 154 displays the current programming parameters and permits the physician to reprogram the parameters. To this end, the physician enters appropriate commands via any of the aforementioned input devices and, under control of the CPU 502, the programming commands are converted to specific programming parameters for transmission to the IMD 100 via the telemetry wand 528 to thereby reprogram the IMD 100. Prior to reprogramming specific parameters, the physician may control the external programmer to display any or all of the data retrieved from the IMD 100, including displays of ECGs, displays of electrodes that are candidates as cathodes and/or anodes, and statistical patient information. Any or all of the information displayed by external device 154 may also be printed using a printer 536.

A speaker 544 is included for providing audible tones to the user, such as a warning beep in the event improper input is provided by the physician. Telemetry subsystem 522 may additionally include an input/output circuit 546 which can control the transmission of analog output signals, such as ECG signals output to an ECG machine or chart recorder. Other peripheral devices may be connected to the external device 154 via parallel port 540 or a serial port 542 as well. Although one of each is shown, a plurality of Input Output (IO) ports might be provided.

With the external device 154 configured as shown, a physician or other authorized user can retrieve, process, and display a wide range of information received from the IMD 100 and reprogram the IMD 100, including configurations of CRT pacing parameters, if needed. The descriptions provided herein with respect to FIG. 5 are intended merely to provide an overview of the operation of the example external device 154 and are not intended to describe in detail every feature of the hardware and software of the device and are not intended to provide an exhaustive list of the functions performed by the device.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in the various flow diagrams. It would also be possible to just perform a subset of the steps shown in the various flow diagrams. For another example, it is possible to change the boundaries of some of the block diagrams.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for use by a system including an implantable medical device (IMD) and an external system (ES), wherein the IMD includes an accelerometer and is configured to be implanted in a patient, the method comprising:

the IMD monitoring for arrhythmic episodes and for each arrhythmic episode of at least some a plurality of arrhythmic episodes that are detected by the IMD during a period of time, determining and storing within memory of the IMD a respective device classified arrhythmia (DCA) data set including the following:

(i) respective EGM data indicative of an EGM segment corresponding to the arrhythmic episode, (ii) respective classification data that specifies a type of the arrhythmic episode, and (iii) respective patient activity information and/or patient posture information corresponding to the arrhythmic episode and obtained using the accelerometer of the IMD;

ranking at least some of the plurality of arrhythmic episodes that were detected by the IMD during the period of time, wherein at least some of the ranking is performed based on at least one of the patient activity information and/or the patient posture information obtained using the accelerometer of the IMD;

selecting for clinical review, based on results of the ranking, a subset of the plurality of arrhythmic episodes that were detected by the IMD during the period of time; and the ES causing displaying of the subset that is selected for clinical review based on results of the ranking;

wherein the subset that is selected for clinical review is less than all of the plurality of arrhythmic episodes that were detected by the IMD during the period of time.

2. The method of claim 1, wherein the patient activity information and/or the patient posture information is indicative of at least one of patient activity, patient posture, a change in the patient activity, or a change in the patient posture.

3. The method of claim 1, wherein the ranking includes:

increasing a ranking score for a first one of the arrhythmic episodes when the activity information and/or the posture information obtained for the first one of the arrhythmic episodes increases a probability that the first one of the arrhythmic episodes was a true positive detection of the type of arrhythmic episode specified in the classification data.

4. The method of claim 3, wherein the ranking includes:

decreasing a ranking score for a second one of the arrhythmic episodes when the activity information and/or the posture information obtained for the second one of the arrhythmic episodes increases a probability that the second one of the arrhythmic episodes was a false positive detection of the type of arrhythmic episode specified in the classification data, or when the activity information and/or the posture information obtained for the second one of the arrhythmic episodes decreases a probability that the second one of the arrhythmic episodes was a true positive detection of the type of arrhythmic episode specified in the classification data.

5. The method of claim 1, wherein when the type of the arrhythmic episode is asystole, a ranking score for the arrhythmic episode is increased when the activity information and/or the posture information obtained for the arrhythmic episode specifies at least one of the following:

the patient moved from an upright position to a laying down or slumped position;

an activity level of the patient fell below a threshold level or ceased; or the activity level of the patient included a sudden and transient increase indicative of a fall or fainting.

6. The method of claim 1, wherein:

the ranking is separately performed for each type of arrhythmia of a plurality of different types of arrhythmias; and the selecting for clinical review, based on results of the ranking, is separately performed for each type of arrhythmia.

7. The method of claim 1, wherein:

the selecting for clinical review includes providing for display the EGM segments corresponding to the subset of the plurality of arrhythmic episodes that are selected based on the results of the ranking.

8. The method of claim 1, further comprising:

the IMD wirelessly transmitting at least some of the DCA data sets stored in the memory in accordance with a schedule, in response to an alert condition being met, or in response to a patient initiated transmission; and the ES obtaining the at least some of the DCA data sets wirelessly transmitted by the IMD, directly or indirectly, from the IMD;

wherein the ES performs the ranking and the selecting.

9. A system, comprising:

an implantable medical device (IMD); and an external system (ES);

the IMD and the ES collectively including one or more processors, at least one of which is included in the IMD, and at least one of which is included in the ES;

the IMD including an accelerometer and configured to:

be implanted in a patient;

monitor for arrhythmic episodes; and for each arrhythmic episode of at least some a plurality of arrhythmic episodes that are detected by the IMD during a period of time, determine and store within memory of the IMD a respective device classified arrhythmia (DCA) data set including the following:

(i) respective EGM data indicative of an EGM segment corresponding to the arrhythmic episode, (ii) respective classification data that specifies a type of the arrhythmic episode, and (iii) respective patient activity information and/or patient posture information corresponding to the arrhythmic episode and obtained using the accelerometer of the IMD; and at least one of the one or more processors configured to:

rank at least some of the plurality of arrhythmic episodes that were detected by the IMD during the period of time, wherein at least some of the ranking is performed based on at least one of the patient activity information and/or the patient posture information obtained using the accelerometer of the IMD; and select for clinical review, based on results of the ranking, a subset of the plurality of arrhythmic episodes that were detected by the IMD during the period of time;

where the subset that is selected for clinical review is less than all of the plurality of arrhythmic episodes that were detected by the IMD during the period of time.

10. The system of claim 9, wherein the patient activity information and/or the patient posture information is indicative of at least one of patient activity, patient posture, a change in the patient activity, or a change in the patient posture.

11. The system of claim 9, wherein at least one of the one or more processors is configured to:

increase a ranking score for a first one of the arrhythmic episodes when the activity information and/or the posture information obtained for the first one of the arrhythmic episodes increases a probability that the first one of the arrhythmic episodes was a true positive detection of the type of arrhythmic episode specified in the classification data.

12. The system of claim 11, wherein at least one of the one or more processors is configured to:

decrease a ranking score for a second one of the arrhythmic episodes when the activity information and/or the posture information obtained for the second one of the arrhythmic episodes increases a probability that the second one of the arrhythmic episodes was a false positive detection of the type of arrhythmic episode specified in the classification data, or when the activity information and/or the posture information obtained for the second one of the arrhythmic episodes decreases a probability that the second one of the arrhythmic episodes was a true positive detection of the type of arrhythmic episode specified in the classification data.

13. The system of claim 9, wherein when the type of the arrhythmic episode is asystole, at least one of the one or more processors is configured to increase a ranking score for the arrhythmic episode when the activity information and/or the posture information obtained for the arrhythmic episode specifies at least one of the following:

the patient moved from an upright position to a laying down or slumped position;

an activity level of the patient fell below a threshold level or ceased; or the activity level of the patient included a sudden and transient increase indicative of a fall or fainting.

14. The system of claim 9, wherein at least one of the one or more processors is configured to:

separately rank arrhythmic episodes for each type of arrhythmia of a plurality of different types of arrhythmias; and separately select for clinical review a separate subset of the plurality of arrhythmic episodes for each type of arrhythmia of the plurality of different types of arrhythmias.

15. The system of claim 9, wherein at least one of the one or more processors is configured to:

cause display of the EGM segments corresponding to the subset of the plurality of arrhythmic episodes that are selected for clinical review based on the results of the ranking.

16. The system of claim 9, wherein:

the IMD is configured to wirelessly transmit at least some of the DCA data sets stored in the memory in accordance with a schedule, in response to an alert condition being met, and/or in response to a patient initiated transmission;

the ES is configured to obtain the at least some of the DCA data sets wirelessly transmitted by the IMD, directly or indirectly, from the IMD;

wherein the at least one processor of the ES is configured to:

rank the at least some of the plurality of arrhythmic episodes based on the at least one of the patient activity information and/or the patient posture information; and select the subset for clinical review.

17. A method for reducing a burden associated with clinical review of electrogram (EGM) segments obtained from an implantable medical device (IMD) that includes an accelerometer and is configured to monitor for arrhythmic episodes of a patient within which the IMD is implanted, the method comprising:

obtaining, for each arrhythmic episode of at least some a plurality of arrhythmic episodes that were detected by the IMD during a period of time, the following:

(i) respective EGM data indicative of an EGM segment corresponding to the arrhythmic episode, (ii) respective classification data that specifies a type of the arrhythmic episode, and (iii) respective patient activity information and/or patient posture information corresponding to the arrhythmic episode and obtained using the accelerometer of the IMD;

ranking at least some of the plurality of arrhythmic episodes that were detected by the IMD during the period of time, wherein at least some of the ranking is performed based on at least one of the patient activity information and/or the patient posture information obtained using the accelerometer of the IMD; and selecting for clinical review, based on results of the ranking, a subset of the plurality of arrhythmic episodes that were detected by the IMD during the period of time;

where the subset of the plurality of arrhythmic episodes, that is selected for clinical review, is less than all of the plurality of arrhythmic episodes that were detected by the IMD during the period of time.

18. The method of claim 17, wherein:

the patient activity information and/or the patient posture information is indicative of at least one of patient activity, patient posture, a change in the patient activity, or a change in the patient posture.

19. The method of claim 17, wherein the ranking includes:

increasing a ranking score for a first one of the arrhythmic episodes when the activity information and/or the posture information obtained for the first one of the arrhythmic episodes increases a probability that the first one of the arrhythmic episodes was a true positive detection of the type of arrhythmic episode specified in the classification data; and decreasing a ranking score for a second one of the arrhythmic episodes when the activity information and/or the posture information obtained for the second one of the arrhythmic episodes increases a probability that the second one of the arrhythmic episodes was a false positive detection of the type of arrhythmic episode specified in the classification data, or when the activity information and/or the posture information obtained for the second one of the arrhythmic episodes decreases a probability that the second one of the arrhythmic episodes was a true positive detection of the type of arrhythmic episode specified in the classification data.

20. The method of claim 17, wherein when the type of the arrhythmic episode is asystole, a ranking score for the arrhythmic episode is increased when the activity information and/or the posture information obtained for the arrhythmic episode specifies at least one of the following:

the patient moved from an upright position to a laying down or slumped position;

an activity level of the patient fell below a threshold level or ceased; or the activity level of the patient included a sudden and transient increase indicative of a fall or fainting.

21. The method of claim 17, wherein:

the ranking is separately performed for each type of arrhythmia of a plurality of different types of arrhythmias for which the respective EGM data, the respective classification data and the respective patient activity information and/or patient posture information were obtained; and the selecting for clinical review, based on results of the ranking, is separately performed for each type of arrhythmia of the plurality of different types of arrhythmias for which the respective EGM data, the respective classification data and the respective patient activity information and/or patient posture information were obtained.

22. The method of claim 17, further comprising:

causing displaying of the EGM segments corresponding to the subset that is selected based on the results of the ranking.

* * * * *